(12) United States Patent
Kido et al.

(10) Patent No.: US 8,211,442 B2
(45) Date of Patent: Jul. 3, 2012

(54) MUCOSAL VACCINE ENABLING SWITCHING FROM PRODUCTION OF IGA ANTIBODY TO PRODUCTION OF BOTH OF IGA AND IGG ANTIBODIES

(75) Inventors: Hiroshi Kido, Tokushima (JP); Dai Mizuno, Tokushima (JP)

(73) Assignee: The University of Tokushima, Tokushima (JP)

( * ) Notice: Subject to any disclaimer, the term of this patent is extended or adjusted under 35 U.S.C. 154(b) by 267 days.

(21) Appl. No.: 11/990,001

(22) PCT Filed: Aug. 4, 2006

(86) PCT No.: PCT/JP2006/315515
§ 371 (c)(1),
(2), (4) Date: Apr. 3, 2008

(87) PCT Pub. No.: WO2007/018152
PCT Pub. Date: Feb. 15, 2007

(65) Prior Publication Data
US 2009/0130131 A1 May 21, 2009

(30) Foreign Application Priority Data
Aug. 5, 2005 (JP) ................................ 2005-227504

(51) Int. Cl.
*A61K 39/12* (2006.01)
(52) U.S. Cl. .................................. 424/204.1; 424/278.1
(58) Field of Classification Search .......................... None
See application file for complete search history.

(56) References Cited

U.S. PATENT DOCUMENTS
6,248,329 B1 * 6/2001 Chandrashekar et al. . 424/191.1
2004/0043032 A1 * 3/2004 McKenzie et al. ......... 424/184.1

FOREIGN PATENT DOCUMENTS
WO 00/06198 2/2000
WO 03/035679 * 5/2003

OTHER PUBLICATIONS

Ellis, R.W. (Chapter 29 of "Vaccines" [Plotkin, S.A. et al. (eds) published by W. B. Saunders company (Philadelphia) in 1988.*
The Dictionary of Immunology, Herbert et al eds, Academic Press, 1995.*
Feng et al (Infection and Immunity, 64(1):363-365, 1996).*
Mizuno et al (Journal of Immunology, 176:1122-1130, Jan. 2006).*
Survanta product disclosure.*
J. F. Van Iwaarden et al., "Alveolar Macrophages, Surfactant Lipids, and Surfactant Protein B Regulate the Induction of Immune Responses via the Airways", Am. J. Respir. Cell Mol. Biol., vol. 24, pp. 452-458, 2001.
H. P. Haagsman et al., "Surfactant-Associated Proteins: Functions and Structural Variation", Comparative Biochemistry and Physiology Part A, vol. 129, pp. 91-108, 2001.

* cited by examiner

*Primary Examiner* — Patricia A Duffy
(74) *Attorney, Agent, or Firm* — Wenderoth, Lind & Ponack, L.L.P.

(57) ABSTRACT

In the aim of practical utilization of a safe and effective transnasal/inactivated/mucosal vaccine and establishment of a technology for imparting capacity of producing both of IgA and IgG antibodies to a conventional inactivated vaccine, toxoid, allergen, or the like, a means for prevention and treatment of allergy, and the like, it is intended to provide an antigen-drug vehicle (AD vehicle) enabling transnasal, transmucosal, and transdermal administrations, an inactivated vaccine simultaneously inducing a mucosal immunity and humoral immunity by using the AD vehicle, a production method of the inactivated vaccine, an AD vehicle enabling a switch from induction of selective production of IgA antibody to induction of both of IgA and IgG antibodies, and a transnasal vaccine, a mucosal vaccine, a therapeutic/prophylactic agent for allergy, and the like using the AD vehicle.

2 Claims, 5 Drawing Sheets

SEQUENCE LISTING

<160> NUMBER OF SEQ ID NOS: 30

<210> SEQ ID NO 1
<211> LENGTH: 1146
<212> TYPE: DNA
<213> ORGANISM: Homo sapiens
<220> FEATURE:
<221> NAME/KEY: CDS
<222> LOCATION: (1)..(1143)

<400> SEQUENCE: 1

```
atg gct gag tca cac ctg ctg cag tgg ctg ctg ctg ctg ccc acg        48
Met Ala Glu Ser His Leu Leu Gln Trp Leu Leu Leu Leu Pro Thr
1               5                   10                  15 ctc tgt ggc cca ggc act gct gcc tgg acc acc tca tcc ttg gcc tgt    96
Leu Cys Gly Pro Gly Thr Ala Ala Trp Thr Thr Ser Ser Leu Ala Cys
                20                  25                  30 gcc cag ggc cct gag ttc tgg tgc caa agc ctg gag caa gca ttg cag   144
Ala Gln Gly Pro Glu Phe Trp Cys Gln Ser Leu Glu Gln Ala Leu Gln
            35                  40                  45 tgc aga gcc cta ggg cat tgc cta cag gaa gtc tgg gga cat gtg gga   192
Cys Arg Ala Leu Gly His Cys Leu Gln Glu Val Trp Gly His Val Gly
        50                  55                  60 gcc gat gac cta tgc caa gag tgt gag gac atc gtc cac atc ctt aac   240
Ala Asp Asp Leu Cys Gln Glu Cys Glu Asp Ile Val His Ile Leu Asn
65                  70                  75                  80 aag atg gcc aag gag gcc att ttc cag gac acg atg agg aag ttc ctg   288
Lys Met Ala Lys Glu Ala Ile Phe Gln Asp Thr Met Arg Lys Phe Leu
                85                  90                  95 gag cag gag tgc aac gtc ctc ccc ttg aag ctc ctc atg ccc cag tgc   336
Glu Gln Glu Cys Asn Val Leu Pro Leu Lys Leu Leu Met Pro Gln Cys
            100                 105                 110 aac caa gtg ctt gac gac tac ttc ccc ctg gtc atc gac tac ttc cag   384
Asn Gln Val Leu Asp Asp Tyr Phe Pro Leu Val Ile Asp Tyr Phe Gln
        115                 120                 125 aac cag act gac tca aac ggc atc tgt atg cac ctg ggc ctg tgc aaa   432
Asn Gln Thr Asp Ser Asn Gly Ile Cys Met His Leu Gly Leu Cys Lys
    130                 135                 140 tcc cgg cag cca gag cca gag cag gag cca ggg atg tca gac ccc ctg   480
Ser Arg Gln Pro Glu Pro Glu Gln Glu Pro Gly Met Ser Asp Pro Leu
145                 150                 155                 160 ccc aaa cct ctg cgg gac cct ctg cca gac cct ctg ctg gac aag ctc   528
Pro Lys Pro Leu Arg Asp Pro Leu Pro Asp Pro Leu Leu Asp Lys Leu
```

-continued

|     |     |     |     |     | 165 |     |     |     | 170 |     |     |     | 175 |     |     |      |
| --- | --- | --- | --- | --- | --- | --- | --- | --- | --- | --- | --- | --- | --- | --- | --- | ---  |
| gtc | ctc | cct | gtg | ctg | ccc | ggg | gcc | ctc | cag | gcg | agg | cct | ggg | cct | cac | 576  |
| Val | Leu | Pro | Val | Leu | Pro | Gly | Ala | Leu | Gln | Ala | Arg | Pro | Gly | Pro | His |      |
|     |     | 180 |     |     |     |     | 185 |     |     |     |     | 190 |     |     |     |      |

```
aca cag gat ctc tcc gag cag caa ttc ccc att cct ctc ccc tat tgc      624
Thr Gln Asp Leu Ser Glu Gln Gln Phe Pro Ile Pro Leu Pro Tyr Cys
            195                 200                 205 tgg ctc tgc agg gct ctg atc aag cgg atc caa gcc atg att ccc aag      672
Trp Leu Cys Arg Ala Leu Ile Lys Arg Ile Gln Ala Met Ile Pro Lys
        210                 215                 220 ggt gcg cta gct gtg gca gtg gcc cag gtg tgc cgc gtg gta cct ctg      720
Gly Ala Leu Ala Val Ala Val Ala Gln Val Cys Arg Val Val Pro Leu
225                 230                 235                 240 gtg gcg ggc ggc atc tgc cag tgc ctg gct gag cgc tac tcc gtc atc      768
Val Ala Gly Gly Ile Cys Gln Cys Leu Ala Glu Arg Tyr Ser Val Ile
                245                 250                 255 ctg ctc gac acg ctg ctg ggc cgc atg ctg ccc cag ctg gtc tgc cgc      816
Leu Leu Asp Thr Leu Leu Gly Arg Met Leu Pro Gln Leu Val Cys Arg
            260                 265                 270 ctc gtc ctc cgg tgc tcc atg gat gac agc gct ggc cca agg tcg ccg      864
Leu Val Leu Arg Cys Ser Met Asp Asp Ser Ala Gly Pro Arg Ser Pro
        275                 280                 285 aca gga gaa tgg ctg ccg cga gac tct gag tgc cac ctc tgc atg tcc      912
Thr Gly Glu Trp Leu Pro Arg Asp Ser Glu Cys His Leu Cys Met Ser
290                 295                 300 gtg acc acc cag gcc ggg aac agc agc gag cag gcc ata cca cag gca      960
Val Thr Thr Gln Ala Gly Asn Ser Ser Glu Gln Ala Ile Pro Gln Ala
305                 310                 315                 320 atg ctc cag gcc tgt gtt ggc tcc tgg ctg gac agg gaa aag tgc aag     1008
Met Leu Gln Ala Cys Val Gly Ser Trp Leu Asp Arg Glu Lys Cys Lys
                325                 330                 335 caa ttt gtg gag cag cac acg ccc cag ctg ctg acc ctg gtg ccc agg     1056
Gln Phe Val Glu Gln His Thr Pro Gln Leu Leu Thr Leu Val Pro Arg
            340                 345                 350 ggc tgg gat gcc cac acc acc tgc cag gcc ctc ggg gtg tgt ggg acc     1104
Gly Trp Asp Ala His Thr Thr Cys Gln Ala Leu Gly Val Cys Gly Thr
        355                 360                 365 atg tcc agc cct ctc cag tgt atc cac agc ccc gac ctt tga             1146
Met Ser Ser Pro Leu Gln Cys Ile His Ser Pro Asp Leu
370                 375                 380

<210> SEQ ID NO 2
<211> LENGTH: 381
<212> TYPE: PRT
<213> ORGANISM: Homo sapiens

<400> SEQUENCE: 2

Met Ala Glu Ser His Leu Leu Gln Trp Leu Leu Leu Leu Leu Pro Thr
1               5                   10                  15

Leu Cys Gly Pro Gly Thr Ala Ala Trp Thr Thr Ser Ser Leu Ala Cys
                20                  25                  30

Ala Gln Gly Pro Glu Phe Trp Cys Gln Ser Leu Glu Gln Ala Leu Gln
            35                  40                  45

Cys Arg Ala Leu Gly His Cys Leu Gln Glu Val Trp Gly His Val Gly
        50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95
```

```
Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
            115                 120                 125

Asn Gln Thr Asp Ser Asn Gly Ile Cys Met His Leu Gly Leu Cys Lys
130                 135                 140

Ser Arg Gln Pro Glu Pro Glu Gln Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
            195                 200                 205

Trp Leu Cys Arg Ala Leu Ile Lys Arg Ile Gln Ala Met Ile Pro Lys
210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Asp Asp Ser Ala Gly Pro Arg Ser Pro
            275                 280                 285

Thr Gly Glu Trp Leu Pro Arg Asp Ser Glu Cys His Leu Cys Met Ser
290                 295                 300

Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
            340                 345                 350

Gly Trp Asp Ala His Thr Thr Cys Gln Ala Leu Gly Val Cys Gly Thr
            355                 360                 365

Met Ser Ser Pro Leu Gln Cys Ile His Ser Pro Asp Leu
370                 375                 380

<210> SEQ ID NO 3
<211> LENGTH: 594
<212> TYPE: DNA
<213> ORGANISM: Homo sapiens
<220> FEATURE:
<221> NAME/KEY: CDS
<222> LOCATION: (1)..(591)

<400> SEQUENCE: 3 atg gat gtg ggc agc aaa gag gtc ctg atg gag agc ccg ccg gac tac      48
Met Asp Val Gly Ser Lys Glu Val Leu Met Glu Ser Pro Pro Asp Tyr
1               5                   10                  15 tcc gca gct ccc cgg ggc cga ttt ggc att ccc tgc tgc cca gtg cac      96
Ser Ala Ala Pro Arg Gly Arg Phe Gly Ile Pro Cys Cys Pro Val His
                20                  25                  30 ctg aaa cgc ctt ctt atc gtg gtg gtg gtg gtc ctc atc gtc gtg          144
Leu Lys Arg Leu Leu Ile Val Val Val Val Val Leu Ile Val Val
            35                  40                  45 gtg att gtg gga gcc ctg ctc atg ggt ctc cac atg agc cag aaa cac      192
Val Ile Val Gly Ala Leu Leu Met Gly Leu His Met Ser Gln Lys His
        50                  55                  60
```

```
acg gag atg gtt ctg gag atg agc att ggg gcg ccg gaa gcc cag caa        240
Thr Glu Met Val Leu Glu Met Ser Ile Gly Ala Pro Glu Ala Gln Gln
 65              70                  75                  80 cgc ctg gcc ctg agt gag cac ctg gtt acc act gcc acc ttc tcc atc        288
Arg Leu Ala Leu Ser Glu His Leu Val Thr Thr Ala Thr Phe Ser Ile
                 85                  90                  95 ggc tcc act ggc ctc gtg gtg tat gac tac cag cag ctg ctg atc gcc        336
Gly Ser Thr Gly Leu Val Val Tyr Asp Tyr Gln Gln Leu Leu Ile Ala
            100                 105                 110 tac aag cca gcc cct ggc acc tgc tgc tac atc atg aag ata gct cca        384
Tyr Lys Pro Ala Pro Gly Thr Cys Cys Tyr Ile Met Lys Ile Ala Pro
        115                 120                 125 gag agc atc ccc agt ctt gag gct ctc act aga aaa gtc cac aac ttc        432
Glu Ser Ile Pro Ser Leu Glu Ala Leu Thr Arg Lys Val His Asn Phe
130                 135                 140 cag atg gaa tgc tct ctg cag gcc aag ccc gca gtg cct acg tct aag        480
Gln Met Glu Cys Ser Leu Gln Ala Lys Pro Ala Val Pro Thr Ser Lys
145                 150                 155                 160 ctg ggc cag gca gag ggg cga gat gca ggc tca gca ccc tcc gga ggg        528
Leu Gly Gln Ala Glu Gly Arg Asp Ala Gly Ser Ala Pro Ser Gly Gly
                165                 170                 175 gac ccg gcc ttc ctg ggc atg gcc gtg aac acc ctg tgt ggc gag gtg        576
Asp Pro Ala Phe Leu Gly Met Ala Val Asn Thr Leu Cys Gly Glu Val
            180                 185                 190 ccg ctc tac tac atc tag                                                594
Pro Leu Tyr Tyr Ile
            195

<210> SEQ ID NO 4
<211> LENGTH: 197
<212> TYPE: PRT
<213> ORGANISM: Homo sapiens

<400> SEQUENCE: 4

Met Asp Val Gly Ser Lys Glu Val Leu Met Glu Ser Pro Pro Asp Tyr
 1               5                  10                  15

Ser Ala Ala Pro Arg Gly Arg Phe Gly Ile Pro Cys Cys Pro Val His
                20                  25                  30

Leu Lys Arg Leu Leu Ile Val Val Val Val Val Leu Ile Val Val
            35                  40                  45

Val Ile Val Gly Ala Leu Leu Met Gly Leu His Met Ser Gln Lys His
 50                  55                  60

Thr Glu Met Val Leu Glu Met Ser Ile Gly Ala Pro Glu Ala Gln Gln
 65              70                  75                  80

Arg Leu Ala Leu Ser Glu His Leu Val Thr Thr Ala Thr Phe Ser Ile
                 85                  90                  95

Gly Ser Thr Gly Leu Val Val Tyr Asp Tyr Gln Gln Leu Leu Ile Ala
            100                 105                 110

Tyr Lys Pro Ala Pro Gly Thr Cys Cys Tyr Ile Met Lys Ile Ala Pro
        115                 120                 125

Glu Ser Ile Pro Ser Leu Glu Ala Leu Thr Arg Lys Val His Asn Phe
130                 135                 140

Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Asn Thr Leu Cys Gly Glu Val
            180                 185                 190
```

Pro Leu Tyr Tyr Ile
        195

<210> SEQ ID NO 5
<211> LENGTH: 576
<212> TYPE: DNA
<213> ORGANISM: Homo sapiens
<220> FEATURE:
<221> NAME/KEY: CDS
<222> LOCATION: (1)..(573)

<400> SEQUENCE: 5

| | | | | | | | | | | | | | | | | |
|---|---|---|---|---|---|---|---|---|---|---|---|---|---|---|---|---|
| atg | gat | gtg | ggc | agc | aaa | gag | gtc | ctg | atg | gag | agc | ccg | ccg | gac | tac | 48 |
| Met | Asp | Val | Gly | Ser | Lys | Glu | Val | Leu | Met | Glu | Ser | Pro | Pro | Asp | Tyr | |
| 1 | | | | 5 | | | | | 10 | | | | | 15 | | |
| tcc | gca | gct | ccc | cgg | ggc | cga | ttt | ggc | att | ccc | tgc | tgc | cca | gtg | cac | 96 |
| Ser | Ala | Ala | Pro | Arg | Gly | Arg | Phe | Gly | Ile | Pro | Cys | Cys | Pro | Val | His | |
| | | | 20 | | | | | 25 | | | | | 30 | | | |
| ctg | aaa | cgc | ctt | ctt | atc | gtg | gtg | gtg | gtg | gtc | ctc | atc | gtc | gtg | | 144 |
| Leu | Lys | Arg | Leu | Leu | Ile | Val | Val | Val | Val | Val | Leu | Ile | Val | Val | | |
| | | 35 | | | | | 40 | | | | | 45 | | | | |
| gtg | att | gtg | gga | gcc | ctc | ctc | atg | ggt | ctc | cac | atg | agc | cag | aaa | cac | 192 |
| Val | Ile | Val | Gly | Ala | Leu | Leu | Met | Gly | Leu | His | Met | Ser | Gln | Lys | His | |
| | 50 | | | | | 55 | | | | | 60 | | | | | |
| acg | gag | atg | gtt | ctg | gag | atg | agc | att | ggg | gcg | ccg | gaa | gcc | cag | caa | 240 |
| Thr | Glu | Met | Val | Leu | Glu | Met | Ser | Ile | Gly | Ala | Pro | Glu | Ala | Gln | Gln | |
| 65 | | | | | 70 | | | | | 75 | | | | | 80 | |
| cgc | ctg | gcc | ctg | agt | gag | cac | ctg | gtt | acc | act | gcc | acc | ttc | tcc | atc | 288 |
| Arg | Leu | Ala | Leu | Ser | Glu | His | Leu | Val | Thr | Thr | Ala | Thr | Phe | Ser | Ile | |
| | | | | 85 | | | | | 90 | | | | | 95 | | |
| ggc | tcc | act | ggc | ctc | gtg | gtg | tat | gac | tac | cag | cag | ctg | ctg | atc | gcc | 336 |
| Gly | Ser | Thr | Gly | Leu | Val | Val | Tyr | Asp | Tyr | Gln | Gln | Leu | Leu | Ile | Ala | |
| | | | 100 | | | | | 105 | | | | | 110 | | | |
| tac | aag | cca | gcc | cct | ggc | acc | tgc | tgc | tac | atc | atg | aag | ata | gct | cca | 384 |
| Tyr | Lys | Pro | Ala | Pro | Gly | Thr | Cys | Cys | Tyr | Ile | Met | Lys | Ile | Ala | Pro | |
| | | 115 | | | | | 120 | | | | | 125 | | | | |
| gag | agc | atc | ccc | agt | ctt | gag | gct | ctc | act | aga | aaa | gtc | cac | aac | ttc | 432 |
| Glu | Ser | Ile | Pro | Ser | Leu | Glu | Ala | Leu | Thr | Arg | Lys | Val | His | Asn | Phe | |
| | 130 | | | | | 135 | | | | | 140 | | | | | |
| cag | gcc | aag | ccc | gca | gtg | cct | acg | tct | aag | ctg | ggc | cag | gca | gag | ggg | 480 |
| Gln | Ala | Lys | Pro | Ala | Val | Pro | Thr | Ser | Lys | Leu | Gly | Gln | Ala | Glu | Gly | |
| 145 | | | | | 150 | | | | | 155 | | | | | 160 | |
| cga | gat | gca | ggc | tca | gca | ccc | tcc | gga | ggg | gac | ccg | gcc | ttc | ctg | ggc | 528 |
| Arg | Asp | Ala | Gly | Ser | Ala | Pro | Ser | Gly | Gly | Asp | Pro | Ala | Phe | Leu | Gly | |
| | | | | 165 | | | | | 170 | | | | | 175 | | |
| atg | gcc | gtg | aac | acc | ctg | tgt | ggc | gag | gtg | ccg | ctc | tac | tac | atc | tag | 576 |
| Met | Ala | Val | Asn | Thr | Leu | Cys | Gly | Glu | Val | Pro | Leu | Tyr | Tyr | Ile | | |
| | | | 180 | | | | | 185 | | | | | 190 | | | |

<210> SEQ ID NO 6
<211> LENGTH: 191
<212> TYPE: PRT
<213> ORGANISM: Homo sapiens

<400> SEQUENCE: 6

Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
            20                  25                  30

Leu Lys Arg Leu Leu Ile Val Val Val Val Val Leu Ile Val Val
        35                  40                  45

Val Ile Val Gly Ala Leu Leu Met Gly Leu His Met Ser Gln Lys His
            50                  55                  60

Thr Glu Met Val Leu Glu Met Ser Ile Gly Ala Pro Glu Ala Gln Gln
 65                  70                  75                  80

Arg Leu Ala Leu Ser Glu His Leu Val Thr Thr Ala Thr Phe Ser Ile
                 85                  90                  95

Gly Ser Thr Gly Leu Val Val Tyr Asp Tyr Gln Gln Leu Leu Ile Ala
            100                 105                 110

Tyr Lys Pro Ala Pro Gly Thr Cys Cys Tyr Ile Met Lys Ile Ala Pro
        115                 120                 125

Glu Ser Ile Pro Ser Leu Glu Ala Leu Thr Arg Lys Val His Asn Phe
130                 135                 140

Gln Ala Lys Pro Ala Val Pro Thr Ser Lys Leu Gly Gln Ala Glu Gly
145                 150                 155                 160

Arg Asp Ala Gly Ser Ala Pro Ser Gly Gly Asp Pro Ala Phe Leu Gly
                165                 170                 175

Met Ala Val Asn Thr Leu Cys Gly Glu Val Pro Leu Tyr Tyr Ile
                180                 185                 190

<210> SEQ ID NO 7
<211> LENGTH: 12
<212> TYPE: PRT
<213> ORGANISM: Homo sapiens

<400> SEQUENCE: 7

Leu Ile Lys Arg Ile Gln Ala Met Ile Pro Lys Gly
 1               5                  10

<210> SEQ ID NO 8
<211> LENGTH: 10
<212> TYPE: PRT
<213> ORGANISM: Homo sapiens

<400> SEQUENCE: 8

Leu Leu Asp Thr Leu Leu Gly Arg Met Leu
 1               5                  10

<210> SEQ ID NO 9
<211> LENGTH: 30
<212> TYPE: PRT
<213> ORGANISM: Homo sapiens

<400> SEQUENCE: 9

Cys Pro Val His Leu Lys Arg Leu Leu Ile Val Val Val Val Val Val
 1               5                  10                  15

Leu Ile Val Val Val Ile Val Gly Ala Leu Leu Met Gly Leu
            20                  25                  30

<210> SEQ ID NO 10
<211> LENGTH: 20
<212> TYPE: PRT
<213> ORGANISM: Homo sapiens

<400> SEQUENCE: 10

Met Ala Glu Ser His Leu Leu Gln Trp Leu Leu Leu Leu Pro Thr
 1               5                  10                  15

Leu Cys Gly Pro
            20

<210> SEQ ID NO 11
<211> LENGTH: 9

```
<212> TYPE: PRT
<213> ORGANISM: Homo sapiens

<400> SEQUENCE: 11

Val Leu Pro Leu Lys Leu Leu Met Pro
1               5

<210> SEQ ID NO 12
<211> LENGTH: 9
<212> TYPE: PRT
<213> ORGANISM: Homo sapiens

<400> SEQUENCE: 12

Tyr Phe Pro Leu Val Ile Asp Tyr Phe
1               5

<210> SEQ ID NO 13
<211> LENGTH: 7
<212> TYPE: PRT
<213> ORGANISM: Homo sapiens

<400> SEQUENCE: 13

Ile Cys Met His Leu Gly Leu
1               5

<210> SEQ ID NO 14
<211> LENGTH: 15
<212> TYPE: PRT
<213> ORGANISM: Homo sapiens

<400> SEQUENCE: 14

Pro Leu Leu Asp Lys Leu Val Leu Pro Val Leu Pro Gly Ala Leu
1               5                   10                  15

<210> SEQ ID NO 15
<211> LENGTH: 80
<212> TYPE: PRT
<213> ORGANISM: Homo sapiens

<400> SEQUENCE: 15

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met Asp
65                  70                  75                  80

<210> SEQ ID NO 16
<211> LENGTH: 8
<212> TYPE: PRT
<213> ORGANISM: Homo sapiens

<400> SEQUENCE: 16

His Leu Cys Met Ser Val Thr Thr
1               5

<210> SEQ ID NO 17
<211> LENGTH: 14
<212> TYPE: PRT
<213> ORGANISM: Homo sapiens
```

```
<400> SEQUENCE: 17

Ile Pro Gln Ala Met Leu Gln Ala Cys Val Gly Ser Trp Leu
1               5                   10

<210> SEQ ID NO 18
<211> LENGTH: 8
<212> TYPE: PRT
<213> ORGANISM: Homo sapiens

<400> SEQUENCE: 18

Pro Gln Leu Leu Thr Leu Val Pro
1               5

<210> SEQ ID NO 19
<211> LENGTH: 24
<212> TYPE: PRT
<213> ORGANISM: Homo sapiens

<400> SEQUENCE: 19

Thr Thr Cys Gln Ala Leu Gly Val Cys Gly Thr Met Ser Ser Pro Leu
1               5                   10                  15
Gln Cys Ile His Ser Pro Asp Leu
            20

<210> SEQ ID NO 20
<211> LENGTH: 35
<212> TYPE: PRT
<213> ORGANISM: Homo sapiens

<400> SEQUENCE: 20

Phe Gly Ile Pro Cys Cys Pro Val His Leu Lys Arg Leu Leu Ile Val
1               5                   10                  15
Val Val Val Val Leu Ile Val Val Ile Val Gly Ala Leu Leu
            20                  25                  30
Met Gly Leu
        35

<210> SEQ ID NO 21
<211> LENGTH: 25
<212> TYPE: PRT
<213> ORGANISM: Homo sapiens

<400> SEQUENCE: 21

Phe Pro Ile Pro Leu Pro Tyr Cys Trp Leu Cys Arg Ala Leu Ile Lys
1               5                   10                  15
Arg Ile Gln Ala Met Ile Pro Lys Gly
            20                  25

<210> SEQ ID NO 22
<211> LENGTH: 41
<212> TYPE: PRT
<213> ORGANISM: Homo sapiens

<400> SEQUENCE: 22

Ala Met Ile Pro Lys Gly Ala Leu Ala Val Ala Val Ala Gln Val Cys
1               5                   10                  15
Arg Val Val Pro Leu Val Ala Gly Gly Ile Cys Gln Cys Leu Ala Glu
            20                  25                  30
Arg Tyr Ser Val Ile Leu Leu Asp Thr
        35                  40
```

```
<210> SEQ ID NO 23
<211> LENGTH: 17
<212> TYPE: PRT
<213> ORGANISM: Homo sapiens

<400> SEQUENCE: 23

Arg Met Leu Pro Gln Leu Val Cys Arg Leu Val Leu Arg Cys Ser Met
1               5                   10                  15

Asp

<210> SEQ ID NO 24
<211> LENGTH: 60
<212> TYPE: PRT
<213> ORGANISM: Homo sapiens

<400> SEQUENCE: 24

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr
    50                  55                  60

<210> SEQ ID NO 25
<211> LENGTH: 19
<212> TYPE: PRT
<213> ORGANISM: Homo sapiens

<400> SEQUENCE: 25

Phe Gly Ile Pro Cys Cys Pro Val His Leu Lys Arg Leu Leu Ile Val
1               5                   10                  15

Val Val Val

<210> SEQ ID NO 26
<211> LENGTH: 20
<212> TYPE: PRT
<213> ORGANISM: Artificial Sequence
<220> FEATURE:
<223> OTHER INFORMATION: Synthtic oligopeptide

<400> SEQUENCE: 26

Lys Leu Leu Leu Leu Lys Leu Leu Leu Lys Leu Leu Leu Leu Leu Lys
1               5                   10                  15

Leu Leu Leu Leu
            20

<210> SEQ ID NO 27
<211> LENGTH: 22
<212> TYPE: PRT
<213> ORGANISM: Artificial
<220> FEATURE:
<223> OTHER INFORMATION: Description of artificial sequence: Synthetic
      oligopeptide

<400> SEQUENCE: 27

Pro Val His Leu Lys Arg Leu Leu Leu Leu Leu Leu Leu Leu Leu Leu
1               5                   10                  15

Leu Leu Leu Leu Leu Leu
            20

<210> SEQ ID NO 28
```

```
<211> LENGTH: 33
<212> TYPE: PRT
<213> ORGANISM: Artificial Sequence
<220> FEATURE:
<223> OTHER INFORMATION: Synthetic oligopeptide

<400> SEQUENCE: 28

Ile Pro Cys Cys Pro Val His Leu Lys Arg Leu Lys Leu Leu Leu
1               5                   10                  15

Leu Leu Leu Leu Ile Leu Leu Leu Ile Leu Gly Ala Leu Leu Met Gly
            20                  25                  30

Leu

<210> SEQ ID NO 29
<211> LENGTH: 34
<212> TYPE: PRT
<213> ORGANISM: Artificial Sequence
<220> FEATURE:
<223> OTHER INFORMATION: Synthetic oligopeptide

<400> SEQUENCE: 29

Gly Ile Pro Phe Phe Pro Val His Leu Lys Arg Leu Lys Leu Leu Leu
1               5                   10                  15

Leu Leu Leu Leu Leu Ile Leu Leu Leu Ile Leu Gly Ala Leu Leu Ile
            20                  25                  30

Gly Leu

<210> SEQ ID NO 30
<211> LENGTH: 35
<212> TYPE: PRT
<213> ORGANISM: Artificial Sequence
<220> FEATURE:
<223> OTHER INFORMATION: Synthetic oligopeptide

<400> SEQUENCE: 30

Phe Gly Ile Pro Ser Ser Pro Val His Leu Lys Arg Leu Leu Ile Leu
1               5                   10                  15

Lys Leu Leu Leu Leu Lys Ile Leu Leu Leu Lys Leu Gly Ala Leu Leu
            20                  25                  30

Ile Gly Leu
        35
```

MUCOSAL VACCINE ENABLING SWITCHING FROM PRODUCTION OF IGA ANTIBODY TO PRODUCTION OF BOTH OF IGA AND IGG ANTIBODIES

TECHNICAL FIELD

This invention relates to an antigen-drug (AD) vehicle enabling transnasal, transmucosal, and transdermal administration and a method for inducting mucosal immunity and humoral immunity using the AD vehicle, more specifically, to an AD vehicle enabling a switch from induction of selective production of IgA antibody to induction of production of both of IgA and IgG antibodies and a transnasal vaccine, a mucosal vaccine, a therapeutic/prophylactic agent of allergy, and the like using the AD vehicle.

BACKGROUND ART

The following drawbacks have been known with conventional inactivated vaccines and toxoids:
(1) Poor infection prevention in natural infection route: In contrast to a vaccine inoculation route which is subcutaneous, intramuscular, or the like, the natural infection route of bacteria, virus, and the like is the mucosae of nostrils, tracheal tract, intestinal tract, and the like, for example, which is different from the inoculation route. There is a demand for realization of infection prevention via inoculation route adapted to the actual condition of natural infection, particularly of mucosal infection prevention by mucosal vaccination.
(2) Low mucosal immunity: In vaccinated subjects, immunoglobulin G (hereinafter abbreviated to IgG or IgG antibody) is mainly produced in the blood to induce humoral immunity. However, since secretory immunoglobulin A (hereinafter abbreviated to IgA or IgA antibody) responsible for mucosal immunity is scarcely produced, it is difficult to expect establishment of mucosal immunity. Necessity and effectiveness of IgA antibody are as follows: IgA antibody is responsible for infection prevention at the mucosae which are portals of droplets and airborne infections into the respiratory organ such as nostrils and tracheal tract as well as oral infection into intestinal tract, i.e. for mucosal immunity, and acts a considerably important role in clinical immunology. Further, in contrast to the IgG antibody that has high specificity to antibody and narrow infection prevention spectrum and is almost ineffective for infection prevention against antigenically varied pathogen, the secretory IgA antibody has cross-immunization property, i.e. cross-neutralization activity; therefore, the secretory IgA antibody has a wider infection prevention spectrum due to the cross-neutralization activity and prevents the infection with variant antigen.
(3) Necessity of additional inoculation and mounting cost: Since it is difficult to expect reliable effect only by primary immunization due to low IgG antibody production by one inoculation, it is necessary to increase a blood IgG antibody value by one or more additional inoculations, i.e. by a so-called booster inoculation, based on IgG antibody retention state after the primary immunization. Therefore, expenses and labor are repeatedly required, and, though the effect is observed with elderly, adults, and school children who have opportunities of booster inoculation, the effect is not achieved in some cases with younger children who tend to miss such opportunities, particularly with infants under 2 years old.

To summarize the above-described situation, the conventional inactivated vaccines, toxoids, and the like have the function and effect of enhancing humoral immunity mainly by inducing production of IgG antibody in the blood of vaccinated subjects, and the efficacy thereof has been confirmed. However, since the conventional inactivated vaccines and toxoids have the low IgA antibody production and low mucosal immunity-inducing capacity, they have a limit from the viewpoints of satisfactory function and effect for preventing natural infection. Under the circumstances, many attempts have been made in various aspects for solving the drawbacks of conventional vaccines. For example, there have been qualitative and quantitative improvements of vaccine antigen, experimental production of live vaccine to replace inactivated vaccine, developments of new inoculation route, mucosal vaccine, and the like, screening on adjuvants capable of realizing enhancement of humorous immunization and maintenance of the enhanced humorous immunization, experiments oriented to development of mucosal immunity adjuvant, and the like. However, development of safe and effective mucosal vaccine has not been achieved yet.

Hereinafter, the development of mucosal vaccine will be described.
(1) Increase in amount of vaccine antigen: Attempts have been made for increasing amounts of IgG and IgA antibodies to be secreted to the mucosae by increasing an amount of a vaccine antigen to be subcutaneously or intramuscularly inoculated. For example, attempts have been made for increasing an antibody production amount by adding neuraminidase of a virus membrane protein to a conventional inactivated influenza vaccine, a method of adding MF59 as an adjuvant, and the like. However, such methods have problems such as pain, strong side reaction, and the like.
(2) Transnasal administration type inactivated vaccine: For the infection prevention by secretory IgA antibody, which is considered most effective, a method of directly inoculating a liquid split antigen via transnasal inoculation has been tried, but a low IgA production amount is pointed out with the method. Accordingly, in order to raise the IgA antibody producibility, a cholera toxin is added as an adjuvant to the split antigen to raise a mucosal immunological response, i.e. the IgA antibody producibility; however, due to the current situation where safety of the toxin as adjuvant is not ensured, practical utilization thereof has not been realized. Also, a split transnasal inactivated influenza vaccine using an *Escherichia coli* bacteria heat-liable toxin as an adjuvant [product of Beruna Biotech (Switzerland), trade name: Nasalflu] was admitted in Switzerland as a world's first nasal influenza vaccine and has been marketed from October, 2000. However, since Bell's palsy was detected in 25.2% of the vaccinated subjects in a vaccinated subject group, clinical usage thereof was banned in February, 2004 (Non-Patent Documents 1 and 2).
(3) Live vaccine using a cold-acclimated strain capable of intranasal inoculation: a live vaccine [product of MedImmuneV/Accines (USA), trade name: FluMist] for intranasally inoculating a cold-acclimated influenza virus (mixture of 3 strains including two type-A strains and a type-B strain, each of the strains is a reassortant) has been admitted and marketed from June, 2003 in USA (Non-Patent Document 3). An optimum temperature for proliferation of the cold-acclimated strain viruses is 25° C., and the viruses do not proliferate at 37° C. (type-B strain) nor 39° C. (type-A strains). However, since a mechanism of toxin attenuation of the cold-acclimated parent strains has not been clarified, the risk of toxin reversion cannot be denied. Further, though the vaccine is excellent for initialization of immunization due to its capability of penetrating into cells due to its active ingredient which is the live virus, mild influenza symptoms sporadically occur due to the vaccine. Therefore, the vaccine has drawbacks such as unavailability for high-risk human, elderly, and the like who are subject to severe symptoms when infected with influenza, unproven effectiveness against frequent continuous drifts and discontinuous shift of influenza virus antigen, and the like.

(4) Other vaccines: Though developments of vector vaccines using a vaccinia virus as a virus vector, attenuated live vaccines employing reverse genetics, DNA vaccines using DNA or cDNA as it is as an active ingredient, and the like have been experimentally conducted, none of them has been put into practical use.

Further, developments of immune adjuvants will hereinafter be described.

(1) Immune adjuvant: An immune adjuvant is a collective term used for substances having modulating activities such as enhancement and suppression of immunological response, and the substances are broadly classified into two categories of those having a dosage form aimed for sustained release, retention, and the like of an antigen in an inoculated subject and those used for enhancement and suppression of immunological response. Among these adjuvants, vaccines and toxoids using aluminum phosphate, alum, and the like have been practically used as the former adjuvant for the dosage form. However, practical utilization of the latter adjuvant for reinforcement and enhancement of immunological response has not been reported. For example, though a bacteria-derived BCG live bacteria, BCG-CWS, endotoxin, glucan and the like, synthetic muramyl dipeptide, levamisole, polyI-polyC, bestatin, and the like, cytokines such as interferon, TNS, and CSF, and the like have been publicly known, it is considered that assurance about safety and effectiveness are required for practical utilization of such adjuvants for the reasons of adjuvant diseases such as arthritis, chronic rheumatoid arthritis, high γ-globulinemia and anemia, insufficient effect, and the like. Also, though a technology (Patent Document 1 and Non-Patent Document 4) of using a pulmonary surfactant protein B derived from higher animal as an adjuvant in order to broadly reinforce induction of humoral immunity has been publicly known, practical utilization thereof has not been reported.

(2) Development of adjuvant for mucosal immunity: Though various adjuvants such as pertusis toxin B oligomer (Patent Document 2), cholera toxin (Patent Document 3), *Escherichia coli* bacteria heat-liable enterotoxin B subunit LTB (Patent Document 4), starch particles (Patent Document 5), cholera toxin B chain protein CTB (Patent Document 6), B subunit of verotoxin 1 (Patent Document 7), oligonucleotide (Patent Document 8), interleukin 12 (Non-Patent Document 7), chitosan (Non-Patent Document 5), and neisserial solubilized surface protein (Non-Patent Document 6) have been developed, none of them has been put into practical use.

As described in the foregoing, the necessity of a switch from the conventional vaccine to be inoculated subcutaneously, intramuscularly, or the like to the mucosal vaccine inducing production of IgA antibody at the mucosae which are the natural virus infection routes is widely and deeply recognized. Particularly, though development and practical utilization of the so-called mucosal vaccine as a new generation vaccine in 21st century for inducing production of IgA antibody and local immunity or mucosal immunity are expected worldwide, such mucosal vaccine has not been achieved. It is considered that the mucosal vaccine has not been achieved since a safe and effective adjuvant for imparting the function of inducing IgA antibody production and local immunity or mucosal immunity has not been specified nor established.

Patent Document 1: JP-T-2002-521460
Patent Document 2: JP-A-3-135923
Patent Document 3: JP-T-10-500102
Patent Document 4: JP-T-2001-523729
Patent Document 5: JP-T-2002-50452
Patent Document 6: JP-A-2003-116385
Patent Document 7: JP-A-2003-50452
Patent Document 8: PCT WO00/20039 pamphlet
Non-Patent Document 1: New Engl. J. Med., Vol. 350, pages 896-903, 2004
Non-Patent Document 2: New Engl. J. Med., Vol. 350, pages 860-861, 2004
Non-Patent Document 3: Cleve. Clin. J. Med., Vol. 70, pages 801-806, 2003
Non-Patent Document 4: Am. J. Respir. Cell Mol. Biol., Vol. 24, 452-458, 2001
Non-Patent Document 5: AdV/Ances Drug Delivery Rev., Vol. 51, pages 81-96, 2001
Non-Patent Document 6: V/Accine, Vol. 21, 3706-3712, 2003
Non-Patent Document 7: Infection and Immunity, Vol. 71, pages 4780-4788, 2003
Non-Patent Document 8: J. neonatal Nursing, Vol. 10, pages 2-11, 2004
Non-Patent Document 9: Biology of the Neonate, Vol. 74 (suppl1), pages 9-14, 1998

DISCLOSURE OF INVENTION

Problems that the Invention is to Solve

It is aimed to impart not only a function of inducing IgA antibody production and local immunity or mucosal immunity but also a function of inducing IgG antibody production or humoral immunity to conventional inactivated vaccines, toxoids, allergens, and the like. It is intended to establish a safe and effective technology for the above-described aim, a safe and effective technology for switching from the conventional humoral immunity-inducing vaccines to vaccine for inducing both of mucosal immunity and humoral immunity, a prophylactic/therapeutic means for allergy, and the like.

Means for Solving the Problems

This invention provides an AD vehicle enabling transnasal, transmucosal, and transdermal administrations, a method for inducing mucosal immunity and humoral immunity using the AD vehicle, more specifically, an AD vehicle enabling a switch from induction of selective production of IgA antibody to induction of production of both of IgA and IgG antibodies and a transnasal vaccine, a mucosal vaccine, a therapeutic/prophylactic agent for allergy, and the like using the AD vehicle.

Effect of the Invention

Application and generalization of the AD vehicle to be provided by this invention enable realization and diffusion of a mucosal vaccine, a prophylactic/therapeutic agent for allergy, and transmucosal/transdermal drug administration. The transnasal/mucosal vaccine exhibits a considerably excellent infection prevention effect as compared to conventional vaccines since it is an immunization means adapted to the actual condition of natural infection. Also, mucosal IgA and IgG in nostrils induced by the AD vehicle causes inactivation of an allergen at the site to enable hyposensitization.

Further, application of the AD vehicle to various drugs reinforces and promotes prophylactic/therapeutic effects by transmucosal administration and transdermal administration of the drugs.

Consequently, this invention greatly improves medical practice/healthcare/hygiene of all humankind and is much-anticipated good news for workers in the fields of medical practice/healthcare/hygiene in the world. Further, this invention renders a means for imparting a function and capability of enabling transmucosal administration and transdermal administration which are simpler than injection to biological drugs including conventional and future vaccines, toxoids, and the like and other various drugs.

BRIEF DESCRIPTION OF DRAWINGS

In FIGS. 1 to 3, an amount of the antibody is a quantitative value by ELISA; n=8 to 12; an average value is ±SD; significance level to a SURFACTEN (Pulmonary Surfactant)-free (0 μg) vaccine administration group by t-test; + indicates $p<0.08$; ++ indicates $p<0.05$; +++ indicates $p<0.01$; * indicates a significance level to a 0.1 μg-SURFACTEN (Pulmonary Surfactant)-added vaccine administration group and $p<0.01$.

FIG. 2 A graph showing an influence exerted on production amounts of anti-influenza IgA and IgG antibodies at the alveolar mucosa by quantity variation of SURFACTEN (Pulmonary Surfactant) to be added to a constant amount (0.2 μg by dry weight) of a vaccine.

FIG. 3 A graph showing an influence exerted on production amounts of anti-influenza IgA and IgG antibodies in the blood by quantity variation of SURFACTEN (Pulmonary Surfactant) to be added to a constant amount (0.2 μg by dry weight) of a vaccine.

In FIGS. 4 to 6: □ indicates an IgA production amount; ■ indicates an IgG production amount; an antibody amount is a quantitative value by ELISA; number of mice of a vaccine administration group is n=4; an average value is ±SD (standard deviation); significance level to the AD vehicle-free vaccine administration group by t-test; + indicates $p<0.01$; and ++ indicates $p<0.05$.

FIG. 5 A graph showing production amounts of anti-influenza IgA and IgG antibodies in lung wash specimens of mice of a control group (no vaccine administration), a vaccine administration group (AD vehicle-free vaccine), an artificial synthetic surfactant (a variation of synthetic AD vehicle)-added vaccine administration group, and a SURFACTEN (Pulmonary Surfactant)-added vaccine administration group.

FIG. 6 A graph showing production amounts of anti-influenza IgA and IgG antibodies in the bloods (serums) of mice of a control group (no vaccine administration), a vaccine administration group (AD vehicle-free vaccine), an artificial synthetic surfactant (a variation of synthetic AD vehicle)-added vaccine administration group, and a SURFACTEN (Pulmonary Surfactant)-added vaccine administration group.

BEST MODE FOR CARRYING OUT THE INVENTION

Figure 1:
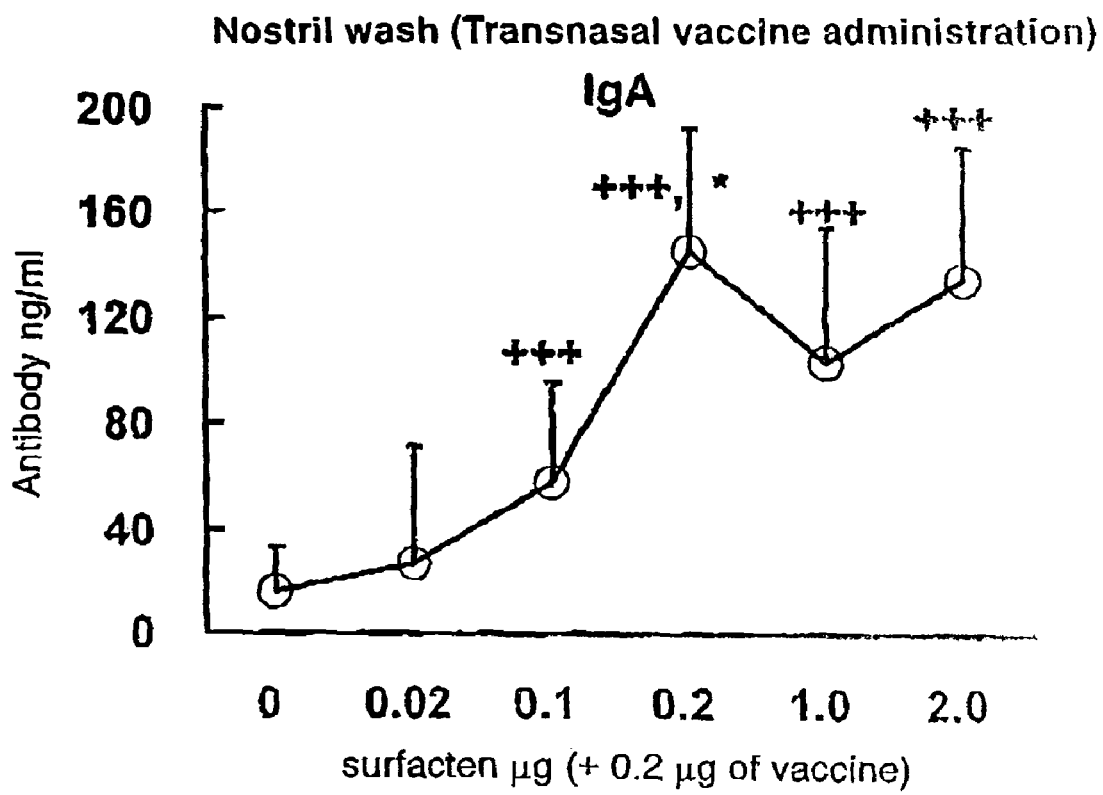
FIG. 1 A graph showing an influence on production amounts of anti-influenza IgA and IgG antibodies at the nasal mucosa by quantity variation of SURFACTEN (Pulmonary Surfactant) (a variation of AD vehicle) to be added to a constant amount (0.2 μg by dry weight) of a vaccine.
Figure 1:
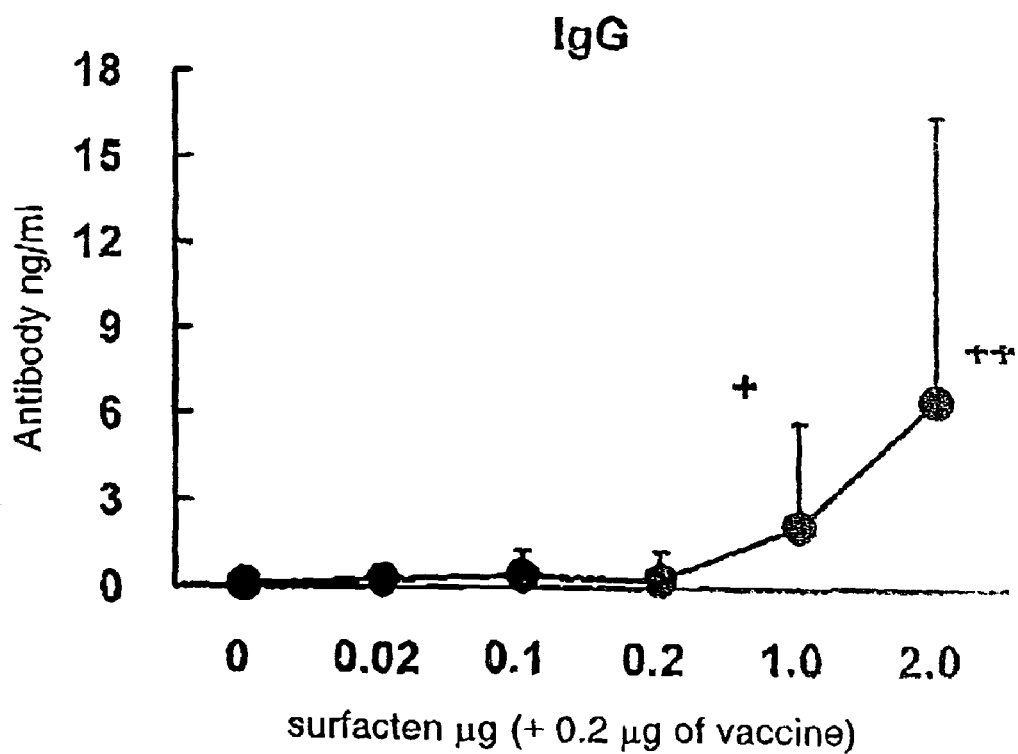

Hereinafter, terms used in this invention and this specification will be described and defined.
(Description of Terms and Antigen-drug (AD) Vehicle Components)
(1) AD vehicle: The vehicle (antigen-drug vehicle; hereinafter referred to as AD vehicle) is a complex of a lipid and a protein designed to enable transmucosal administration and transdermal administration of an antigen, a drug, and the like. The AD vehicle is formed of the following (a) and/or (b) and (c):
(a) a pulmonary surfactant protein B or a fragment thereof (including not only a natural fragment obtainable by protease, but also an artificial fragment obtainable by gene engineering and peptide synthesis, a variant fragment obtainable by conversion and/or deletion of one or more of amino acids forming the fragments, and the like);
(b) a pulmonary surfactant protein C or a fragment thereof (including not only a natural fragment obtainable by protease, but also an artificial fragment obtainable by gene engineering and peptide synthesis, a variant fragment obtainable by conversion and/or deletion of one or more of amino acids forming the fragments, and the like); and
(c) a lipid such as phospholipid and aliphatic acid.

The AD vehicle has the shape and structure of a membrane (sheet-like or rolled lipid membrane) that has on its surface a spine-like or spike-like polypeptide chain, and terminals in hydrophobic areas of a plurality of polypeptide chains are transplanted as being fitted into the lipid membrane in the form of spikes to make the lipid membrane different from conventional liposomes. By causing a desired antigen, drug, or the like to coexist with, contact, capture, adhere to, or combine with (mount on) the AD vehicle according to this invention, transmucosal administration and transdermal administration of the antigen, drug, or the like is enabled. In other words, the vehicle is a vehicle for an antigen, a drug, or the like, which enables the transmucosal administration and transdermal administration of the antigen, drug, or the like.

Details of the components of the AD vehicle and the proteins, the polypeptides or peptides and lipids to be used for preparation/production of the vehicle, i.e. the pulmonary surfactant-derived SP-B, SP-C, the fragments thereof, the variant fragments and the like obtained by conversion and/or deletion of one or more of amino acids forming the fragments, and the lipid such as phospholipid and aliphatic acid will be described later in this specification.
(2) Pulmonary surfactant: The pulmonary surfactant has been put into practical use from 1987 for respiratory distress syndrome (RDS) therapy, and, at present, there are reports on pulmonary surfactants that are derived from human, cow, pig, and the like, among which drugs of the cow-derived and pig-derived pulmonary surfactants are commercially available and in common use (Non-Patent Document 8). Also, a synthetic peptide drug containing an active domain related to RDS therapy has been commercially available, and, further, design developments and syntheses of SP-B and SP-C analogues are in progress (Non-Patent Document 9).

A composition and a structure of the pulmonary surfactant are: a complex formed of about 90 wt % of lipids (67.3% of phosphatidylcholine, 19.3% of phosphatidylglycerol, 3.2% of phosphatidylserine, other free aliphatic acids, and the like) and about 10 wt % of proteins (surfactant proteins A, B, C, and D; hereinafter abbreviated to SP-A, SP-B, SP-C, and SP-D). Molecular amounts of SP-A, SP-B, SP-C, and SP-D are 26 to 38 kDa, 5 to 8 kDa, 4 to 5 kDa, and 43 kDa, respectively. SP-A and SP-D are hydrophilic (water-soluble) and lectin-like (membrane associated). SP-B and SP-C are hydrophobic (liposoluble) and have a lipid-binding property, capability of fitting into the phospholipid membrane, and a surface-activating property. Pulmonary surfactant protein genes derived from human, cow, pig, and the like are publicly known, and, in GenBank/NCBI (www.ncbi.nlm.nih.gov), accession numbers of full-length base sequences of human SP-B gene DNA and human SP-C (and SP-C1) gene DNA are J02761 and J03890. Hereinafter, coding regions (CDR) of the human SP-B and SP-C obtained from NCBI and amino acid sequences encoded thereby are described.

SEQ ID NO 1: CDR base sequence of human SP-B gene DNA;

SEQ ID NO 2: Human SP-B full-length amino acid sequence identified from SEQ ID NO: 1;

SEQ ID NO 3: CDR base sequence of human SP-C gene DNA;

SEQ ID NO 4: Human SP-C full-length amino acid sequence identified from SEQ ID NO: 3;

SEQ ID NO 5: CDR base sequence of SP-C1 in human SP-C gene DNA;

SEQ ID NO 6: Human SP-C1 full-length amino acid sequence identified from SEQ ID NO: 5.

In a living body, SP-B exists as molecules formed of 80 (or 79 or 81) amino acid residues 201 to 280 (also reported as to 279 or 281) in the amino acid sequence of SEQ ID NO: 2. SP-C exists as molecules formed of 35 amino acid residues 24 to 58 in SEQ ID NO: 4 or 6.

(3) Protein or peptide to be used in this invention: For preparation and production of the AD vehicle according to this invention, a combination of SP-B and SP-C and a combination of SP-B and SP-C1 derived from a mammal such as human, cow, horse, sheep, pig, whale, dolphin, or the like may be used. For example, a human-derived protein consisting of the full-length amino acid sequence set forth in any one of SEQ ID NOs: 2, 4, and 6, a combination of SP-B and SP-C, or a combination of SP-B and SP-C1 may be used. Further, a hydrophobic (liposoluble) region of SP-B and SP-C based on hydrophobic value of Kyte-Doolittle, a fragment including the region, a variant fragment obtained by conversion and/or deletion of at least one amino acid of the fragment peptide, and the like may be used. For example, natural peptides consisting of amino acid sequences set forth in SEQ ID NOs: 7 to 20 shown below or peptides obtainable by gene engineering or chemical synthesis, longer peptides including such peptides, mutants or synthetic analogues obtained by conversion and/or deletion of at least one amino acid of the peptides, and the like may be used. The amino acid numbers are represented by ordinal numbers by setting Met at N-terminal of each of the sequences as the first amino acid and in the order toward C-terminal direction (from left to right in the described sequence). Also, in the SP-B fragment, the polypeptide included in the amino acids 201-280 in the amino acid sequence of SEQ ID NO: 2 is referred to as "SP-B(1-80) fragment", for example, by setting the 201st Phe as the first amino acid. Likewise, the SP-C fragment is referred to as "SP-C(1-35) fragment", for example, by setting the 24th Phe in SEQ ID NO: 4 as the first amino acid.

SEQ ID NO 7: Amino acid sequence consisting of 214th to 225th amino acids of SEQ ID NO: 2 (SP-B fragment);

SEQ ID NO 8: Amino acid sequence consisting of 226th to 275th amino acids of SEQ ID NO: 2 (SP-B fragment);

SEQ ID NO 9: Amino acid sequence consisting of 29th to 58th amino acids of SEQ ID NOs: 4 and 6 (SP-C fragment);

SEQ ID NO 10: Amino acid sequence consisting of 1st to 20th amino acids of SEQ ID NO: 2 (SP-B fragment);

SEQ ID NO 11: Amino acid sequence consisting of 102nd to 110th amino acids of SEQ ID NO: 2 (SP-B fragment);

SEQ ID NO 12: Amino acid sequence consisting of 119th to 127th amino acids of SEQ ID NO: 2 (SP-B fragment);

SEQ ID NO 13: Amino acid sequence consisting of 136th to 142nd amino acids of SEQ ID NO: 2 (SP-B fragment);

SEQ ID NO 14: Amino acid sequence consisting of 171st to 186th amino acids of SEQ ID NO: 2 (SP-B fragment);

SEQ ID NO 15: Amino acid sequence consisting of 201st to 280th amino acids of SEQ ID NO: 2 (SP-B (1-80) fragment);

SEQ ID NO 16: Amino acid sequence consisting of 300th to 307th amino acids of SEQ ID NO: 2 (SP-B fragment);

SEQ ID NO 17: Amino acid sequence consisting of 317th to 330th amino acids of SEQ ID NO: 2 (SP-B fragment);

SEQ ID NO 18: Amino acid sequence consisting of 344th to 351st amino acids of SEQ ID NO: 2 (SP-B fragment);

SEQ ID NO 19: Amino acid sequence consisting of 358th to 381st amino acids of SEQ ID NO: 2 (SP-B fragment);

SEQ ID NO 20: Amino acid sequence consisting of 24th to 58th amino acids of SEQ ID NOs: 4 and 6 (SP-C(1-35) fragment);

SEQ ID NO 21: Amino acid sequence consisting of 201st to 225th amino acids of SEQ ID NO: 2 (SP-B(1-25) fragment);

SEQ ID NO 22: Amino acid sequence consisting of 220th to 260th amino acids of SEQ ID NO: 2 (SP-B(20-60) fragment);

SEQ ID NO 23: Amino acid sequence consisting of 264th to 280th amino acids of SEQ ID NO: 2 (SP-B(64-84) fragment);

SEQ ID NO 24: Amino acid sequence consisting of 201st to 260th amino acids of SEQ ID NO: 2 (SP-B(1-60) fragment);

SEQ ID NO 25: Amino acid sequence consisting of 24th to 42nd amino acids of SEQ ID NOs: 4 and 6 (SP-C(1-19) fragment);

SEQ ID NO 26: KL-4 (synthetic peptide modeled on SP-B);

SEQ ID NO 27: SP-CL [synthetic SP-C(7-28) fragment];

SEQ ID NO 28: SP-C 33 (SP-C type synthetic peptide);

SEQ ID NO 29: SP-C(FFI) [synthetic peptide wherein 28th and 29th amino acid residues CC of the SP-C(25-58) fragment are replaced by FF, and 56th amino acid residue M is replaced by I]; and SEQ ID NO 30: SP-C(KLS) (hybrid (fused) type synthetic peptide modeled on SP-B and SP-C).

According to this invention, it is possible to use a combination of (a) at least one selected from SP-B consisting of the amino acid sequences set forth in SEQ ID NOs: 2, 7, 8, and 10 to 24 and the fragments thereof and/or (b) at least one selected from SP-C consisting of the amino acid sequence set forth in SEQ ID NOs: 4, 6, 9, 20, 25, and 26 and the fragments thereof, i.e. Group (a) alone, Group (b) alone, or the combination of Groups (a) and (b). Also, in the case of selecting the combination of two or more of SP-B, SP-C, or the fragments thereof, SP-B, SP-C, or the fragments thereof may be mixed or may be formed into a fused protein (fused peptide).

(4) Lipid used in this invention: As the phospholipid, phospholipid contained in the pulmonary surfactant, such as phosphatidylcholine, dipalmitoylphosphatidylcholine, and phosphatidylserine may preferably be used. Other than the above phospholipids, diacylglycerophosphoglycerol, phosphatidylglycerol, dilauroylphosphatidylglycerol, dimyristoylphosphatidylglycerol, dipalmitoylphosphatidylglycerol, distearoylphosphatidylglycerol, phosphatidylinositol, phosphatidylethanolamine, phosphatidic acid, sphingomyelin, and the like may be used. Also, as the aliphatic acid, lauric acid, myristic acid, palmitic acid, stearic acid, palmitoleic acid, oleic acid, and the like may be used. Further, lipid derived from an aquatic animal having active lung inflation such as whale, tuna, and dolphin may be used.

(5) Pulmonary surfactant drugs reported as for use in RSD therapy: According to this invention, a reported pulmonary surfactant admitted by relevant authorities in view of safety and effective as the RDS therapeutic agent and containing hydrophobic or liposoluble SP-B, SP-C, and phospholipid, such as SURFACTEN, INFASURF, CUROSURF, HUMANSURF, EXOSURF, ALVEOFACT, and SURFACXIN (Pulmonary Surfactants) may be used as the AD vehicle. The commercially available drugs containing hydrophilic or water soluble SP-A and SP-D in addition to the SP-B and SP-C are used after being subjected to extraction of the water-soluble proteins SP-A and SP-D by using 1-butanol to eliminate the proteins to an amount lower than the detection limit. Also, in view of adjustment of a concentration in preparing the AD vehicle, a dry formulation is preferred to a liquid formulation.

This invention has been accomplished as a result of the exquisite observation and analytic skills, profound knowledge, and innovative idea of the first inventor who endured much trials and tribulations for more than 10 years in the above-described violent and severe background and is based on the following astonishing findings:

(1) Though conventional adjuvants that enhances antigen presentation capacity by causing inflammation, the inventor has found that, when a complex of a combination of SP-B and SP-C obtained by eliminating SP-A and SP-D from SP-A, SP-B, SP-C, and SP-D that are four protein active ingredients of a pulmonary surfactant which is a surface-activating substance secreted originally from the pulmonary mucosa and gut mucosa and phospholipid or a complex (above-described AD vehicle) of a combination of synthetic peptides of both of SP-B and SP-C fragments including liposoluble regions (active regions) of SP-B and SP-C and a lipid membrane is allowed to coexist with, contact, capture, or adhere to a virus antigen, antigen presentation cells of the nasal mucosa are activated without causing of inflammation resulting in efficient virus antigen uptake by the cells and effective and preferential induction of anti-virus IgA production at the mucosae without inducing IgG production in the mucosae and blood.

(2) The inventor has found that, by adding the complex of a combination of SP-B and SP-C and phospholipid or the complex (AD vehicle) of a combination of synthetic peptides of both of SP-B and SP-C fragments including liposoluble regions (active regions) of SP-B and AP-C and a lipid membrane to an influenza virus split antigen that has heretofore been used as a safe inactivated vaccine antigen, selective induction of IgA production is realized in a state where the high safety of the split antigen is maintained and antigen presentation cell activation is sufficiently increased as compared to antigen presentation cell activation achieved by the split antigen alone which is inferior to that of live vaccines.

(3) Further, as a result of analysis relating to immunity induction capacity of a transnasal/mucosal vaccine prepared by mounting a split influenza virus vaccine antigen on the AD vehicle, the inventor has found that the selective induction of IgA production depends on a weight ratio V/A between an AD vehicle dry mass (V; note that a lipid weight or a phospholipid weight may be used as the value V since lipid or phospholipid ordinarily occupies about 90 wt % or more of the AD vehicle dry mass) and a vaccine antigen dry weight (A) and reached to amazing findings that the IgA production is selectively induced when V/A is 1 or less, while production of both of IgA and IgG is induced when V/A exceeds 1.

The facts that lead to this invention are as follows.

(1) The first inventor has conducted extensive research to clarify the pathogenic mechanism of and therapeutic/prophylactic method for influenza. In the course of the research, the inventor has clarified that a pulmonary surfactant absorbs tryptase clara of HA processing protease of the respiratory tract to ultimately inhibit a virus proliferation cycle, the tryptase clara being responsible for limited proteolysis of hemagglutinin (HA) of an influenza virus membrane protein and causing the virus to develop membrane-fusion activity and infectious ability.

(2) As a result of subsequent studies, the inventor has found that the pulmonary surfactant has a function of causing induction of secretory IgA by activating immunocompetence for the virus antigen by selectively activating antigen presentation cells of the mucosae and not causing induction of IgG in addition of the above-described function. Further, the inventor has clarified that SP-B and SP-C are important as mucosal immunity-enhancing active ingredients in the pulmonary surfactants in addition to the lipid components and investigated on identification of active regions and effectiveness of the mucosal immunity enhancement of the protein components.

(3) Further, the inventor has carried forward his study from the viewpoints of a biologic defense substance at the respiratory mucosa and virus infection prevention to prove that the pulmonary surfactant secreted in a living body is involved in the induction of selective IgA production as a mucosal immunity adjuvant derived from the living body.

(4) The inventor has conducted further studies by noting on the fact that the pulmonary surfactant originally is a physiologically active substance in a living body and that (a) has a characteristic of absorbing a specific biological substance [Kido, et al., FEBS Lett., 322(29), 115-119, 1992], (b) is secreted from the alveolar type II cells and clara cells and selectively taken up by macrophage to be metabolized (Akira Suwabe, J. Jpn. Med. Soc. Biol. Interface, 33, 10-13, 2002), and (c) is taken up by analogous cells of the above cells, such as antigen presentation cells (dendritic cells) to be metabolized.

As a result, the inventor has clarified that SP-B, SP-C, and the lipid component among the protein components of the pulmonary surfactant function as the AD vehicle of a mucosal vaccine selectively inducing IgA production, and that an active ingredient region or a mucosal immunity-inducing active domain of SP-B is a peptide consisting of the following amino acid sequences:

SP-B 214-225:
(SEQ ID NO: 7)
Leu Ile Lys Arg Ile Gln Ala Met Ile Pro Lys Gly; and SP-B 257-266:
(SEQ ID NO: 8)
Leu Leu Asp Thr Leu Leu Gly Arg Met Leu.

Also, the inventor has clarified that an active ingredient region or a mucosal immunity-inducing active domain of SP-C is a peptide consisting of the following amino acid sequence:

```
SP-C 29-58:
                                          (SEQ ID NO: 9)
Cys Pro Val His Leu Lys Arg Leu Leu Ile Val Val

Val Val Val Val Leu Ile Val Val Val Ile Val Gly

Ala Leu Leu Met Gly Leu.
```

(5) As a mechanism of the selective IgA induction, the inventor has clarified that the active ingredients of the pulmonary surfactant promote class switch to IgA-producing B-lymphocytes by inducing local mucosal cytokine TGF-β1 in addition to the effective antigen presentation to T-lymphocytes achieved by inducing increased expression of MHC Class II, CD40, and B7-2 of the antigen presentation dendritic cells.

(6) The inventor has reached to the findings that a switch for converting from the selective induction of IgA production to the induction of production both of IgA and IgG exists in an immune function by the transnasal/mucosal vaccine which is prepared by mixing a split influenza virus vaccine antigen and the AD vehicle, and that the switch depends on the weight ratio V/A between the AD vehicle amount (V) and the vaccine antigen amount (A). In the case where a relatively large amount of vaccine antigen (15 mg/Kg or more) is transnasally inoculated, both of IgA for mucosal immunity and IgG for systemic immunity are induced irrespective of the V/A amount ratio.

Objects of this invention that has been accomplished based on the above-described findings and facts are as follows:

(1) The first object is to establish a mucosal immunization method. It is intended to realize selective induction of production of antigen-specific IgA which is an active ingredient for mucosal immunization and a transnasal/mucosal vaccine inducing production of both of IgA and IgG through provision and use of the AD vehicle as well as to establish a safe and effective (free from adverse reaction) induction of mucosal immunity and a method therefor.

(2) The second object is a quality improvement through the use of the synthetic peptides from the viewpoints of safety, effectiveness, homogeneity of the AD vehicles. It is intended to improve the quality of AD vehicles by providing the complexes (AD vehicles) prepared by using the synthetic peptide of SP-B mucosal immunity-inducing active domain (consisting of the amino acid sequences of SP-B 214-225 and SP-B 257-266), the synthetic peptide of SP-C mucosal immunity-inducing active domain (consisting of the amino acid sequence of SP-C 29-58), the synthetic analogues thereof, or the long chain synthetic peptides containing a part of the amino acid sequences and the pulmonary surfactant lipid components.

(3) The third object is a change from subcutaneous inoculation to transmucosal administration of the conventional vaccines. It is intended to convert subcutaneous inoculation vaccines into mucosal vaccines by using the AD vehicles for inactivated vaccines for respiratory tract infection viruses, such as inactivated vaccines for influenza, SARS, measles, rubella, mumps, and the like and inactivated vaccines for intestinal tract infection viruses, such as inactivated vaccines for rota, polio, and the like.

(4) The fourth object is to provide a method for using the AD vehicles for inactivated vaccines for virus infections via mucosae other than the respiratory and intestinal tracts, such as inactivated vaccines for AIDS, hepatitis B, hepatitis C, and the like.

(5) The fifth object is to provide a method for using the AD vehicles for DNA vaccines, live vaccines, prophylaxis and therapy for allergy, and the like.

(6) The sixth object is to provide a method for using the AD vehicles for transdermal inoculations (embrocation, patching, etc.) as immunization routes capable of inducing IgA in addition to the transmucosal inoculations.

(7) The seventh object is to develop usages and applications of the AD vehicles not only for drug delivery system and drug preparation but also for agriculture, fishery, and the like.

The AD vehicles proposed by this invention are different from the conventional adjuvants used in the field of immunology in property and effect as described below.

The conventional adjuvants are ordinarily subcutaneously or intramuscularly inoculated to cause a local inflammation reaction and contain as an active ingredient a foreign matter that attracts antigen presentation cells and B- or T-lymphocytes to cause the cells to manifest their capabilities. Further, in order to maintain the inflammation reaction for a long time, a mineral oil and a metal salt that cause sustained release and retention of the antigen are used in combination. Those known as the conventional mucosal vaccine/adjuvant are foreign matters such as the *Escherichia coli* bacteria heat-liable toxin and cholera toxin as described above and subject to a risk of causing harmful action and adverse reaction.

In contrast, the AD vehicles according to this invention do not cause the local inflammation reaction. Further, the AD vehicles are derived from the biological component, and the active ingredients and active domains in the pulmonary surfactant are specified, thereby realizing effective mucosal vaccines by using the domains and low molecular peptides containing the domain regions. Therefore, the AD vehicles are remarkably safe and uninvasive.

According to this invention, the following (1) to (8) are provided:

(1) A mucosal vaccine for inducing both of antibodies IgA and IgG productions, which is obtained by causing an antigen-drug (AD) vehicle to coexist, contact, capture, or absorb an antigen in an amount inducing IgA for mucosal immunity, in which the AD vehicle is a complex comprising at least one protein selected from Group A consisting of a pulmonary surfactant protein B, its fragment and a synthetic peptide modeled on a function structure thereof and/or at least one protein selected from Group B consisting of a pulmonary surfactant protein C, its fragment, and a synthetic peptide modeled on a function structure thereof and at least one lipid selected from Group C consisting of lipids, wherein a weight ratio V/A between a dry mass (V) of the vehicle and a dry mass (A) of the antigen is adjusted to exceed about one.

As used herein, the antigen means an antigen that is highly purified to a purity of about 90% or more to be used for vaccines and derived from a pathogen such as a virus, a toxin, an inactivated antigen, a toxoid, a synthetic epitope region thereof; an allergen, an allergen epitope, a protein, a glycoprotein, a high molecular carbohydrate, nucleic acid, and the like having a purity of about 90% or more; and the like.

Also, the AD vehicle is a complex comprising substances each selected from Group A described below (pulmonary surfactant protein B, a natural fragment and synthetic peptides derived or originated from the protein B) and/or Group B described below (pulmonary surfactant protein C, a natural fragment and synthetic peptides derived or originated from the protein C) and Group C described below (lipids such as phospholipid and aliphatic acid), i.e. the AD vehicle is a complex comprising at least two substances selected respectively from Group A and Group C, a complex comprising at least two substances selected respectively from Group B and Group C, or a complex comprising at least three substances selected respectively from Group A, Group B, and Group C:
<Group A> pulmonary surfactant protein B, a polypeptide consisting of the amino acid sequence 1 to 381 (SEQ ID NO: 2) set forth in SEQ ID NO: 2 (amino acid numbers are assigned by setting Met at N-terminal as the first amino acid and in the order toward C-terminal direction), fragments thereof each including 214 to 225 (SEQ ID NO: 7), 257 to 266 (SEQ ID NO: 8), 1 to 20 (SEQ ID NO: 10), 102 to 110 (SEQ ID NO: 11), 119 to 127 (SEQ ID NO: 12), 136 to 142 (SEQ ID NO: 13), 171 to 185 (SEQ ID NO: 14), 201 to 280 (SEQ ID NO: 15), 300 to 307 (SEQ ID NO: 16), 317 to 330 (SEQ ID NO: 17), 344 to 351 (SEQ ID NO: 18), 358 to 381 (SEQ ID NO: 19), 201 to 225 (SEQ ID NO: 21), 220 to 260 (SEQ ID NO: 22), 264 to 280 (SEQ ID NO: 23), and 201 to 260 (SEQ ID NO: 24), a polypeptide having at least one sequence of the above-described amino acid sequences as an active domain, a polypeptide obtained by conversion and/or deletion of at least one amino acid of each of the amino acid sequences, synthetic peptides or synthetic analogues modeled on function structures of the polypeptides, substances obtained by modifying the polypeptides with a sugar or a sugar chain, such as a synthetic peptide KL-4 modeled on SP-B (SEQ ID NO: 26) and a hybrid (fused) synthetic peptide of SP-B and SP-C (SEQ ID NO: 30), and the like.
<Group B> pulmonary surfactant protein C; polypeptides consisting of the following amino acid sequences set forth in SEQ ID NO: 4 (amino acid numbers are assigned by setting Met at N-terminal as the first amino acid and in the order toward C-terminal direction): 1 to 197 (SEQ ID NO: 4), 1 to 191 (SEQ ID NO: 6), 29 to 58 (SEQ ID NO: 9), 24 to 58 (SEQ ID NO: 20), 24 to 42 (SEQ ID NO: 25); polypeptides consisting of 1-191 amino acid sequence set forth in SEQ ID NO: 6 (amino acid numbers are assigned by setting Met at N-terminal as the first amino acid and in the order toward C-terminal direction); a polypeptide having at least one sequence of the above-described amino acid sequences as an active domain; a polypeptide obtained by conversion and/or deletion of at least one amino acid of each of the amino acid sequences; synthetic peptides or synthetic analogues modeled on function structures of the polypeptides; substances obtained by modifying the polypeptides with a sugar or a sugar chain, such as a synthetic peptide SP-C(7-28) fragment SP-CL (SEQ ID NO: 27), an SP-C type synthetic peptide SP-C33; a synthetic peptide SP-C(FFI) (SEQ ID NO: 29) obtained by replacing the 28th and 29th amino acid residues Cys Cys by Phe Phe and replacing the 56th amino acid residue Met by Ile in an SP-C (25-58) fragment, and a hybrid (fused) synthetic peptide of SP-B and SP-C (SEQ ID NO: 30) that is also listed in Group A, and the like.
<Group C> Lipids including phospholipid such as phosphatidylcholine, dipalmitoylphosphatidylcholine, phosphatidylserine, phosphatidylglycerol, phosphatidylinositol, phosphatidylethanolamine, and phosphatidic acid; aliphatic acid such as lauric acid, myristic acid, palmitic acid, stearic acid, and oleic acid; and the like.
(2) A mucosal vaccine for selectively inducing IgA antibody production, in which the weight ratio V/A between the vehicle amount (V) and the antigen amount (A) in (1) above is adjusted to about one or less.
(3) The mucosal vaccine according to (1) or (2), wherein Group A comprises proteins having the amino acid sequences of SEQ ID NOs: 2, 7, 8, to 19, 21 to 24, 26, and 30.
(4) The mucosal vaccine according to (1), (2) or (3), wherein Group B comprises proteins having the amino acid sequences of SEQ ID NOs: 4, 6, 9, 20, 25, and 27 to 30.
(5) The mucosal vaccine according to any one of (1) to (4), wherein Group C comprises lipids of phosphatidylcholine, dipalmitoylphosphatidylcholine, phosphatidylserine, phosphatidylglycerol, phosphatidylinositol, phosphatidylethanolamine, phosphatidic acid, lauric acid, myristic acid, palmitic acid, stearic acid, and oleic acid.
(6) The mucosal vaccine according to (1) or (2), wherein the antigen (A) is an inactivated antigen derived from an epidemic pathogen or a detoxified toxin.
(7) A prophylactic/therapeutic agent for allergy, in which the antigen (A) is an allergen, an allergen epitope, or an allergen-derived antigen.
(8) A method for inducing a mucosal immunity, comprises adjusting the weight ratio V/A between the vehicle amount (V) and the antigen amount (A) set forth in claim 1 to about one to use a conversion switch from selective production of IgA antibody to production of both of IgA and IgG antibodies.

Hereinafter, embodiments of this invention will be described.
(1) Composition of AD Vehicle Dry weights by wt % of Group A (pulmonary surfactant protein B and natural and synthetic peptides derived or originated from the protein B) and/or Group B (pulmonary surfactant protein C and natural and synthetic peptides derived or originated from the protein C) and Group C (lipid such as phospholipid and aliphatic acid) are as follows: about 0.1 to about 6.0 wt % of Group A; about 0.1 to about 6.0 wt % of Group B, and about 88 to about 99.8 wt % of Group C. In preparation of the AD vehicle, the composition is adjusted to "Group A (%)+Group B (%)+Group C (%)=100%", "Group A (%)+Group C (%)=100%", or "Group B (%)+Group C (%)=100%" in wt %.
(2) AD Vehicle Preparation Example (Example of Using the Three Groups A, B, and C)

Hereinafter, a preparation procedure will be described. For example, 2 mg of Group A, 2 mg of Group B, and 96 mg of Group C are weighed (group A (%)+group B (%)+group C (%)=100% in wt %), and Groups A, B, and C are uniformly suspended in 5 ml of an isotonic solution such as a normal saline solution and a phosphate buffer saline (PBS). The thus-obtained suspension is used as an AD vehicle (100 mg/5 ml) solution. The vehicle is prepared in each use. For the suspension preparation, a supersonic wave, a homogenizer, a mixer, a shaking apparatus, or the like may be used.

Since the supersonic wave tends to cause modification (increase in viscosity) of the liquid due to excessive processing, it is desirable to use a mixer such as a box mixer [e.g. Vortex Mixer (trade name)].

As the 96 mg of lipid (Group C), a mixture of 71 mg of phosphatidylcholine, 21 mg of phosphatidylglycerol, and 4 mg of phosphatidylserine or the like may be used (the total lipid amount is 96 mg). Also, in the case of using a pulmonary surfactant drug for RDS therapy which is reported to contain SP-B and SP-C, such as SURFACTEN and SURFACXIN (Pulmonary Surfactants), it is possible to use a suspension prepared in accordance with the instruction attached thereto as it is as the AD vehicle solution.
(3) Preparation of Mucosal Vaccine: The AD vehicle solution is added to a vaccine stock solution in such a manner that a dry weight ratio V/A of an antigen amount (A) and an AD vehicle amount (V) in a vaccine becomes a desired value. For example, when the weight ratio V/A=1 is applied, an amount of the AD vehicle (50 mg/ml) prepared in (2) to be added to 50 µl of a vaccine stock solution containing 50 mg/ml of an antigen is 50 μl. For the purpose of uniform mixing, a homogenizer, a mixer, a shaking apparatus, a stirrer, or the like may be used.

As used herein, the antigen means a bacteria-derived antigen, a virus antigen, a toxoid, and the like that are highly purified to a purity of about 90% or more, an allergen such as those derived from cedar pollen or mite, a protein, a glycoprotein, a high molecular carbohydrate, nucleic acid, and the like. As the value A as an antigen mass, an actual measurement value or a calculated value of a purity, a specific activity, a molecular amount, an antigen-antibody reaction of the antigen may be used.

As the value V in calculation of the weight ratio V/A, a lipid amount or a phospholipid mass may be used in place of the AD vehicle amount since about 90 wt % of the AD vehicle is lipid or phospholipid in the typical preparation.

The dry weight (A) of the antigen in the mucosal vaccine of this invention may be about 0.1 to about 50 μg/kg, preferably about 0.3 to about 30 μg/kg. A V/A for preferentially and selectively induce IgA production in such antigen amount may preferably be about 0.1 to about 1.0. A V/A for inducing production of both of IgA and IgG may be in the range of about 1.0 to about 100, preferably about 20 to about 50.

A mucosal immunity vaccine obtained by coupling about 60% or more of the antigen to the AD vehicle in the above-described V/A ranges is capable of effectively inducing IgA antigen production and/or IgG antigen production.

Hereinafter, a structure and effects of this invention will be described in detail in conjunction with Reference Examples, Experimental Examples, and Examples. However, this invention is not limited to the specific examples, explanation, and description.

REFERENCE EXAMPLE 1

AD Vehicle Preparations and Samples

Preparations and samples of pulmonary surfactants to be used as AD vehicles in this invention will be hereinafter described. Sample prepared from a cow lung by the method of Howood, et al. (Biochemistry, 24, 184-190, 1985); a sample obtained by eliminating water-soluble protein components SP-A and SD-D through extraction with 1-butanol from the sample or reducing SP-A and SD-D to an amount lower than the detection limit in the sample (Haasman H. P., et al, J. Biol. Chem., 262, 13977-13880, 1987); sample containing 2 or more of lipids selected from 40 wt % or more of phospholipids such as phosphatidylcholine and dipalmitoylphosphatidylcholine, about 10 to 30 wt % of phosphatidylglycerol, about 2 to about 5 wt % of phosphatidylserine, about 1.0 to about 20 wt % of palmitic acid, and the like, a pulmonary surfactant-derived liposoluble (hydrophobic) protein, an active region of SP-B and/or SP-C or a synthetic peptide containing the active region, such as about 0.1 to about 12 wt % of a synthetic peptide formed from an active region of human SP-C (24-58 amino acid sequence set forth in SEQ ID NO: 20) FGIPCCPVHLKRLLIVVVVVVLIVVVIVGALLMGL and prepared to achieve a total amount of the components of 100 wt %; a commercially available or publicly known pulmonary surfactant such as SURFACTEN, INFASURF, CUROSURF, HUMANSURF, EXOSURF, ALVEOFACT, SurfaxinSURFAXIN (Pulmonary Surfactants), and the like.

EXPERIMENTAL EXAMPLE 1

Preparation of Split Influenza Vaccine

By using an embryonated egg-derived suspension [$1\times10^8$ PFU (Plaque Forming Unit)] inoculated with an influenza-A virus strain Aichi/68/2/H3N2 (offered from Dr. Masanobu Ohuchi of Department of Microbiology of Kawasaki Medical School), a split influenza vaccine was prepared by the following operation. To the virus suspension dialyzed overnight with 0.004 M PBS [product of Takara Bio Inc. (Japan)], 0.05 vol % of β-propiolactone [product of Wako Pure Chemical Industries, Ltd. (Japan)] was added to achieve a final concentration of 8 nM, followed by virus inactivation by incubation in an ice bath for 18 hours. Subsequently, β-propiolactone was subjected to hydrolytic degradation by incubation at 37° C. for 1.5 hours. After completion of the hydrolytic degradation, Tween 80 [product of Wako Pure Chemical Industries, Ltd. (Japan)] was added to achieve a final concentration of 0.1 wt %, and diethylether [product of Wako Pure Chemical Industries, Ltd. (Japan)] in an amount equivalent to that of Tween 80 was added, followed by inverted mixing at 4° C. for 2 hours. The thus-obtained liquid was centrifuged at 2,000 rpm for 5 minutes, followed by collection of a supernatant thereof. After eliminating diethylether from the supernatant by using Automatic Environmental Seed V.Ac System [product of SaV/Ant Instrument, INC (USA)], the supernatant was sterilized by filtration using Millex 0.45 μm filter [product of Millipore (USA)] to be used as an inactivated split influenza vaccine stock solution.

EXPERIMENTAL EXAMPLE 2

Preparation of Transnasal/Mucosal Vaccine

The split influenza vaccine stock solution obtained by Experimental Example 1 and the AD vehicle described in Reference Example 1 were mixed. After suspending the AD vehicle into PBS (phosphate buffer saline) until a concentration required for vaccination is achieved, a supersonic wave treatment was performed at a room temperature for 5 minutes to obtain a uniform suspension. To the suspension, 0.1 μg (dry weight) of the vaccine stock solution was added with respect to 0.1 μg (dry weight) of the AD vehicle, followed by mixing with Vortex Mixer, and the mixture was left to stand at a room temperature for one hour to prepare a transnasal/mucosal vaccine for IgA induction. Also, after adding 0.1 μg (dry weight) of the vaccine stock solution with respect to 1.0 μg (dry weight) of the AD vehicle, a transnasal/mucosal vaccine for both of IgA and IgG induction was prepared in the same manner as described above.

EXPERIMENTAL EXAMPLE 3

Animal Experiment 6-week-old female BALB/c mice [purchased from Japan SLC, Inc. (Japan)] were used. All animal experiments were conducted in an infected animal confinement facility (P2 level) of Tokushima University Medical Department Laboratory Animal Center and in accordance with the Tokushima University Medical Department Animal Experiment Committee Guideline.

EXPERIMENTAL EXAMPLE 4

Transnasal Administration

In transnasal administration of the vaccine, the vaccine obtained by Experimental Example 2 was diluted with PBS to achieve a vaccine concentration of 0.1 μg/μl (dry weight), and 1 μl of the diluted vaccine was dropped into each of nostrils of each of the etherized mice to administer 2 μl of the diluted vaccine to each of the mice. To a control group, the same amount (2 μl) of PBS was administered by nasal drip. Secondary immunization was performed by the nasal drip at 4 weeks after the primary immunization, and a nasal wash, an alveolar wash, a blood serum of each of the mice were prepared at 2 weeks after the secondary immunization to be used as specimens for measurements of both of IgA and IgG antibodies specific to the vaccine strain virus.

EXPERIMENTAL EXAMPLE 5

Preparations of Mouse Nasal Wash, Alveolar Wash, and Blood Serum

Each of the vaccinated mice was subjected to thoracotomy and laparotomy under pentobarbital anesthesia, and the trachea was cut to insert an atom knotted vein catheter 3Fr [product of Atom Medical Corporation (Japan)] into the lung, followed by injection of 1 ml of a normal saline solution and collection of the wash. This operation was repeated for three times to obtain 3 ml of washes to be used as an alveolar wash. After collecting the lung wash, an atom vein catheter was inserted from the opened trachea toward the nostrils, and 1 ml of a normal saline solution was injected, and a liquid flowed out of the nostrils was collected. This liquid was used as a nasal wash. Further, blood from the heart was centrifuged at 5,000 rpm for 10 minutes to obtain a supernatant, and the supernatant was used as a blood serum.

EXPERIMENTAL EXAMPLE 6

Quantitative Determination of Protein

A protein content of each of the nasal wash, the lung wash, and the blood serum was measured by using BCA Protein Assay Reagent Kit [product of Peirce (USA)] (Anal. Biochem., 150, 76-85, 1985). Absorbance at 562 nm was measured by using SPECTRA Max PLUS 384 (product of Molecular Devices Corporation (USA)).

EXPERIMENTAL EXAMPLE 7

Purification of IgA and IgG Antibodies Specific to Influenza Virus

For use as a standard or reference for quantitative determination by ELISA, the IgA and IgG antibodies were purified and prepared in the manner described below. By affinity chromatography using recombinant *Escherichia coli* bacteria-expressed protein G sepharose 4B column [product of Zymed Laboratories Inc. (USA)], an IgG fraction was purified from the alveolar wash of each of the influenza-vaccinated and influenza virus-infected mice. Also, an anti-mouse IgA goat IgG antibody [product of Sigma (USA)] was coupled to a BrCN activated sepharose 4B column [product of Amersham Bioscience (USA)], and an IgA fraction was purified from a flow-through fraction of Protein G by means of affinity chromatography using the column. In order to purify virus-specific antibodies from the IgA and IgG fractions, an antigen affinity chromatography, in which the inactivated split influenza vaccine antigen used for the immunization was coupled to a BrCN activated sepharose column, was employed for purification/preparation of each of IgA and IgG antibodies specific to the influenza virus. For the coupling of the split influenza virus antigen protein to the column as a ligand, a coupling reaction was performed by using a 0.1 M $NaHCO_3$/0.5 M NaCl buffer solution (pH 8.5), and the free ligand was eliminated by using 1 M acetic acid/0.5 M NaCl (pH 8.5) and neutralized with PBS (pH 7.5). Each of the affinity chromatographies was performed in such a manner that the affinity coupling reaction and free antibody elimination conducted by using PBS (pH 7.5) followed by elution of the specific antibodies by using a glycine-HCl buffer solution (pH 2.8). The eluted fraction was immediately neutralized with 0.5 M Tris-HCl buffer solution (pH 9.0) and dialyzed with Milli Q water, followed by freeze-drying. The IgA and IgG were dissolved into PBS in each use as standard reagents (antibodies) for ELISA.

EXPERIMENTAL EXAMPLE 8

Quantitative Determination of Anti-Influenza Virus IgA and IgG Antibodies

A content of each of the anti-influenza virus IgA and IgG antibodies in the nasal wash, the alveolar wash, and the blood serum was determined by ELISA. ELISA was performed by using Mouse ELISA quantitatin kit [product of Bethyl Laboratories (USA)]. After adding 1 μg of the vaccine and 100 μg of a PBS solution of a 1 μg/ml-cow serum albumin [BSA; product of Sigma (USA)] to each of wells of a 96 well Nunc immunoplate [product of Nalgen Nunc International (USA)], an immobilization reaction was performed at 4° C. overnight. After that, rinsing with a cleaning liquid (50 mM Tris, 0.14 M NaCl, 0.05 wt % Tween 20, pH 8.0) was performed for three times to eliminate the vaccine liquid. 200 μl of 50 mM Tris-HCL buffer solution (pH 8.0) containing 0.15 M NaCl and 1 wt % BSA was added to each of the wells to allow a blocking reaction at a room temperature for one hour. After rinsing the wells with the cleaning liquid for three times, 100 μl of the nasal wash, the lung wash, or the blood serum diluted to an appropriate amount by using a sample coupling buffer solution (50 mM Tris, 0.15 M NaCl, 0.05 wt % Tween 20, 1 wt % BSA, pH 8.0) was added to allow a reaction at a room temperature for 2 hours. An antibody mouse IgA goat IgG antibody or IgG-horse radish peroxidase [product of Bethyl Laboratories Inc. (USA)] was used as a secondary antibody for performing a chromogenic reaction by TMB Micowell Peroxidase Substrate System [product of Kirkegaard 85 Perry laboratoties, Inc. (USA)]. Subsequently, the reaction was stopped by adding 100 μl of 2 M $H_2SO_4$ [product of Wako Pure Chemical Industries, Inc. (Japan)] to each of the wells, and an absorbance at 450 nm was measured by SPECTRA MAX PLUS 384. Anti-influenza viruses IgA and IgG obtained by purifying the lung wash obtained by Example 7 were used as standard reagents (antibodies) for quantitative determination, and absorbances were measured in the same manner as described above to use the measurement values as standard.

EXAMPLE 1

(1) Preparation of Transnasal/Mucosal Vaccine

SURFACTEN (Pulmonary Surfactant) [product of Mitsubishi Pharma Corporation (Japan)] was used as the AD vehicle, and a mixture of SURFACTEN (Pulmonary Surfactant) and the influenza inactivated vaccine obtained by Example 1 was subjected to supersonic wave treatment to prepare a mucosal vaccine. SURFACTEN (Pulmonary Surfactant) was suspended in use into PBS to achieve a concentration required for vaccination, and a uniform suspension was obtained by a supersonic wave treatment at a room temperature for one minute. Subsequently, the SURFACTEN (Pulmonary Surfactant) suspension was added to 0.2 µg (dry weight) of the vaccine in such a manner that concentrations of the SURFACTEN (Pulmonary Surfactant) by way of a phospholipid amount thereof became 0 (no addition), 0.02 µg, 0.1 µg, 0.2 µg, 1.0 µg, and 2.0 µg, followed by mixing by Vortex Mixer and supersonic wave treatment at a room temperature for 3 minutes. The vaccine liquids were incubated at a room temperature for one hour before administration.

(2) Mouse Immunization

In vaccine transnasal administration, each of the vaccine liquids was diluted with PBS to obtain a solution containing the vaccine in an amount equivalent to 0.1 µg/µl by dry weight, and the diluted vaccine liquid was administered to nostrils of BALB/c mouse for primary immunization. A secondary immunization was performed in the same manner as in the primary immunization at 4 weeks after the primary immunization, and a nasal wash, an alveolar wash, and a blood serum were collected and prepared from each of the mice at 2 weeks after the secondary immunization to be used for quantitative detection of anti-influenza IgA and IgG.

(3) Judgment of Immune Effect

Levels of anti-influenza IgA and IgG in the nasal wash, the alveolar wash, and the blood serum (respective preparation are described in Experimental Example 5) were measured by quantitative detection by ELISA (procedure of ELISA is described in Experimental Example 8), and influences and effects by SURFACTEN (Pulmonary Surfactant) as the AD vehicle to be exerted on induction of mucosal immunity and/or humoral immunity by the transnasal vaccine were evaluated based on results of significant difference test (t-test) of the levels.

Figure 2:
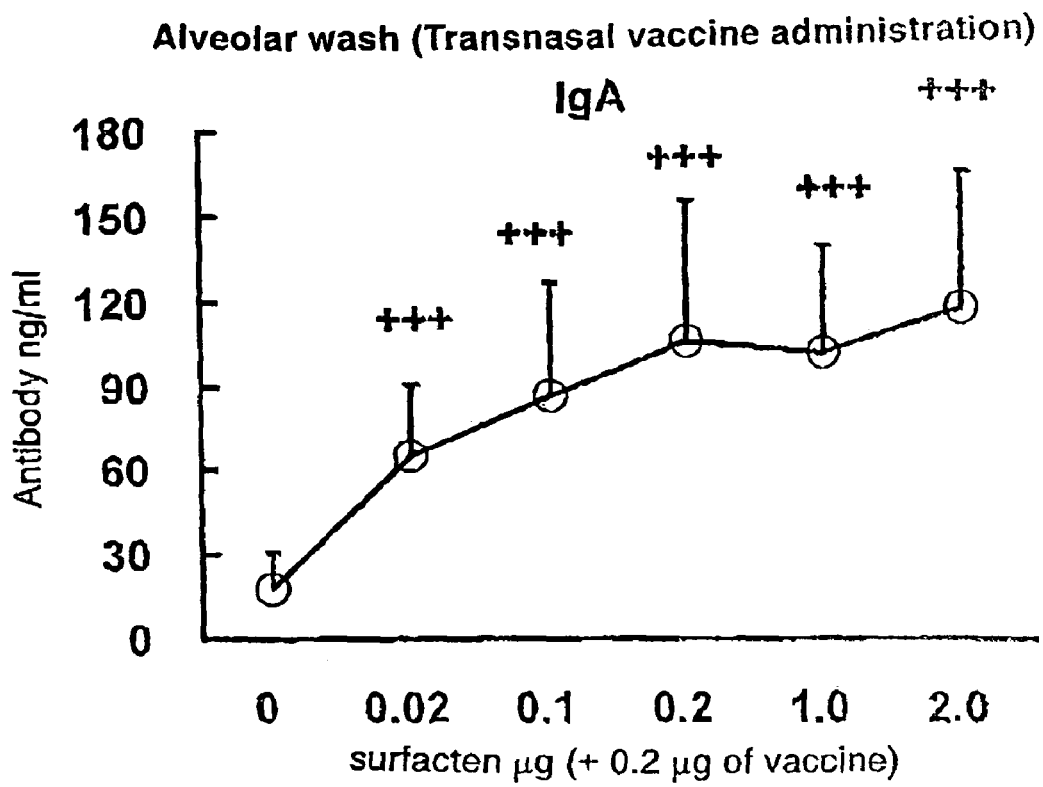
Figure 2:
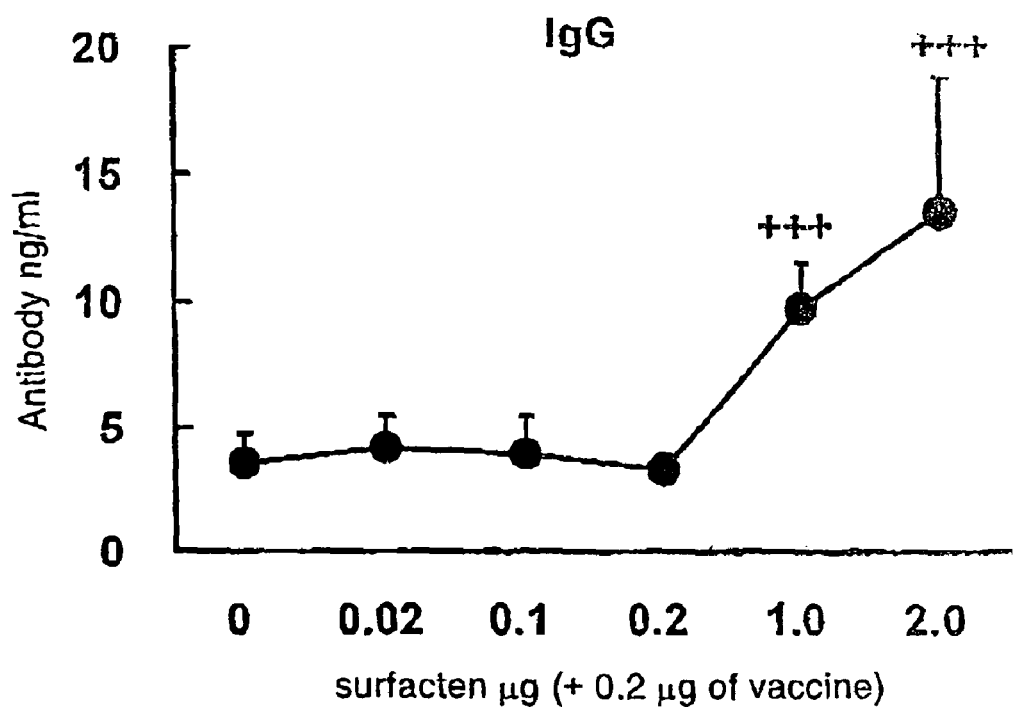

When the amount of SURFACTEN (Pulmonary Surfactant) added to the vaccine was 0.2 µg or less (hereinafter referred to as low dose group), the anti-influenza IgA production amounts at the nasal mucosa and alveolar mucosa were increased depending on the SURFACTEN (Pulmonary Surfactant) amount (FIGS. 1 and 2). However, enhancement associated with the increase in SURFACTEN (Pulmonary Surfactant) was not observed with the IgG production amount in the low dose group, and productions of a blood antibody, IgA, and IgG were not induced (FIG. 3).

Figure 3:
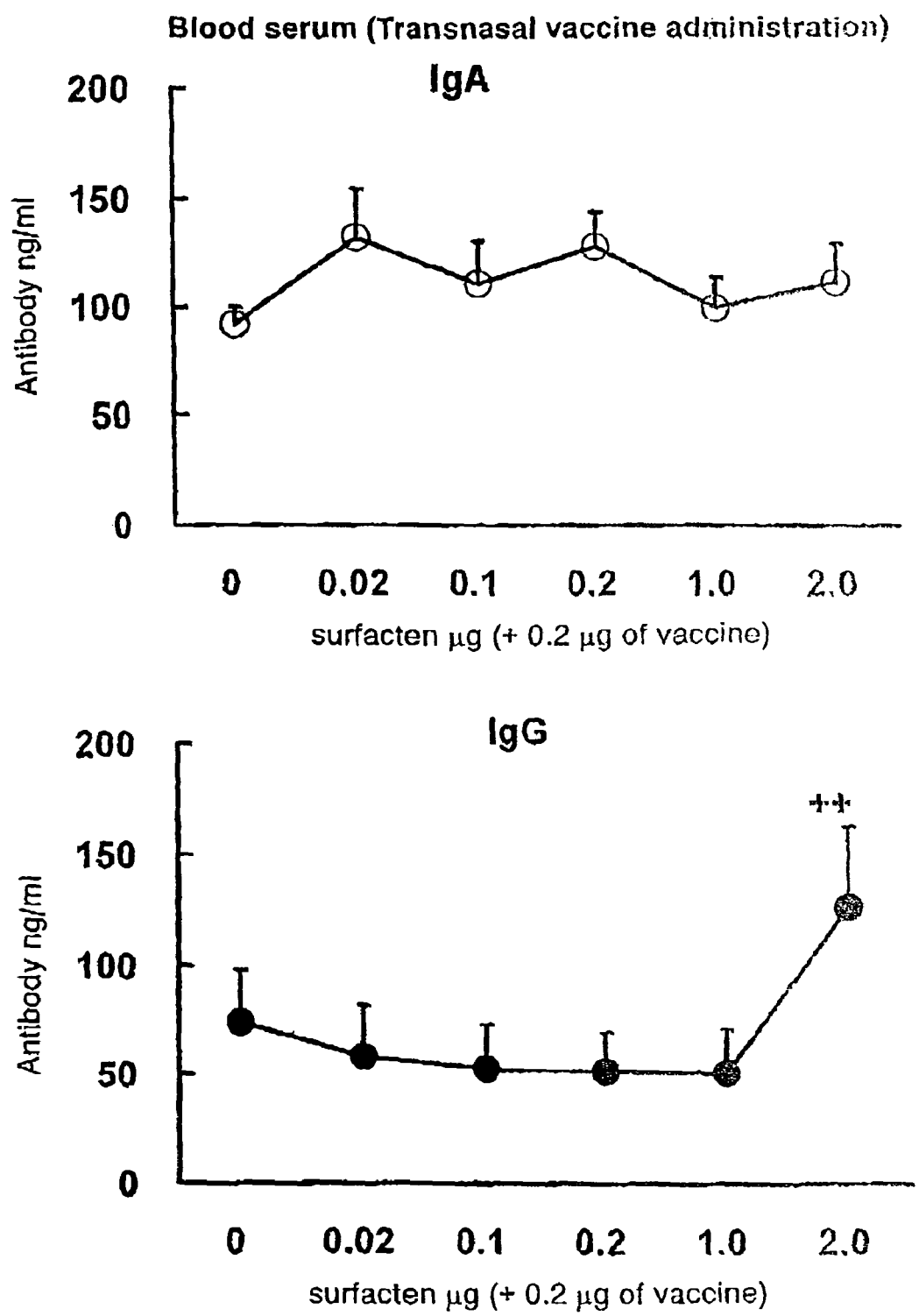

In FIGS. 1 to 3, the number of mice in each of vaccinated groups was n=8 to 12, an average value was ±SD (standard deviation), a significance level was a significance level with respect to the SURFACTEN (Pulmonary Surfactant)-free vaccine-administrated group, + means $p<0.08$, ++ means $p<0.05$, +++ means $p<0.01$, and * means a significance level with respect to the 0.1 µg SURFACTEN (Pulmonary Surfactant)-added group and $p<0.01$.

In contrast, when the SURFACTEN (Pulmonary Surfactant) amount was 1.0 to 2.0 µg (hereinafter referred to as high dose group) the anti-influenza IgG production amounts at the nasal mucosa and the alveolar mucosa were increased depending on the SURFACTEN (Pulmonary Surfactant) amount (see FIGS. 1 and 2). Also, the blood IgG production amount was significantly increased in Group in which SURFACTEN (Pulmonary Surfactant) was used (FIG. 3). Also, in the high dose group, a significant increase in IgA production amount was not observed as compared to that of the low dose group, and enhancement of mucosal immunity effect of the low dose group was not observed (FIGS. 1 and 2).

(4) Specification of Switch from IgA Production to Productions of Both of IgA and IgG Since the above-described results are relativity between the dry vaccine weight (0.2 µg) and the quantity variation (0 to 2.0 µg) of phospholipid in SURFACTEN (Pulmonary Surfactant) (AD vehicle), switch was calculated and specified as a weight ratio of the phospholipid amount/dry vaccine amount in the AD vehicle (hereinafter referred to as V/A) as follows:
(a) IgA was produced when V/A was about 1.0 or less;
(b) both of IgA and IgG were produced when V/A exceeds about 1.0; and
(c) the switch from the IgA production to the production of both of IgA and IgG was specified to be the V/A of about 1.

The phospholipid mass (weight) in the AD vehicle was used for the value V in the V/A calculation. However, since 90 wt % or more of the components of the AD vehicle according to this invention is the phospholipid, it was judged that it is possible to use, in addition to the phospholipid amount, the lipid amount (including phospholipid) or the AD vehicle amount (dry weight) as the value V in adjustment of the weight ratio V/A when carrying out this invention.

EXAMPLE 2

(1) Synthesis of Human Pulmonary Surfactant Protein

The synthetic peptide FGIPCCPVHLKRLLIVVVVVV-LIVVVIVGALLMGL (SEQ ID NO: 20) [synthesized by Greiner Bio-One (Germany)] of an active region of human SP-C having purity of 95% or more was ordered/purchased. A synthetic SP-C suspension was obtained by suspending the synthetic peptide into a CM suspension (buffer solution obtained by mixing chloroform and ethanol at a volumetric ratio of 2:1) to achieve a protein amount thereof of 10 mg/ml, and the synthetic SP-C suspension was used for preparation of an artificial AD vehicle (artificial human pulmonary surfactant) described below.

(2) Preparation of Synthetic AD Vehicle

Preparation of an artificial surfactant having a structure and a function as a pulmonary surfactant was conducted in accordance with the method of Takei, et al. (Biol. Pharm. Bull., 1996, 19, 1247-1253). Specifically, dipalmitoylphosphatidylcholine [product of Wako Pure Chemical Industries, Inc. (Japan)], phosphatidylglycerol, and palmitic acid were mixed in a weight ratio of 75:25:10, and a mixture was suspended into a CM mixture liquid (mixture liquid having a volumetric ratio between chloroform and ethanol of 2:1) to achieve a concentration as a phospholipid amount of 10 mg/ml, thereby obtaining a lipid component suspension.

Trifluoroacetic acid (TFA) in an amount same as that of the SP-C suspension was added to the SP-C suspension to be perfectly dissolved into the SP-C suspension. Subsequently, after adding the lipid component suspension to the SP-C solution until an SP-C amount by a phospholipid weight in the lipid component becomes 2% (w/w), the mixture was dried by using a rotary evaporator at 40° C. The dried mixture was suspended into a 10%-ethanol solution until the phospholipid amount becomes 10 mg/ml, and the suspension was mixed by shaking in a hot water bath of 45° C. for 15 minutes. After freeze-drying the mixture, the mixture was stored as an artificial dried human pulmonary surfactant (synthetic AD vehicle) at −30° C. to −4° C.

(3) Preparation of Transnasal/Mucosal Vaccine

The above-described artificial dried AD vehicle was suspended into PBS to achieve a phospholipid amount of 30 mg/ml, followed by a supersonic wave treatment at a room temperature for one minute to obtain a uniform suspension. The artificial surfactant or SURFACTEN (Pulmonary Surfactant) (described in Example 1) as a positive control of immunization induction effect was added to the suspension to achieve 2.0 μg of the phospholipid amount with respect to 0.2 μg of the vaccine obtained by Example 1, followed by mixing by Vortex Mixer and a supersonic wave treatment at a room temperature for 3 minutes. The thus-obtained transnasal mucosal vaccine was incubated for one hour before administration. The vaccine liquid was diluted with PBS to obtain a 0.1 μg/μl solution of the vaccine to be transnasally administered.

(4) Mouse Immunization

In the same manner as in Example 1, each of BALB/c mice was immunized, and a nasal wash, an alveolar wash, and a blood serum were collected/prepared from each of the mice at 2 weeks after the secondary immunization to be used for quantitative determination of anti-influenza IgA and IgG.

(5) Judgment of Immunization Effect

In the same manner as in Example 1, levels of anti-influenza IgA and IgG were measured by quantitative determination by ELISA, and influences and effects to be exerted on induction of mucosal immunity and/or humoral immunity by the artificial human pulmonary surfactant (synthetic AD vehicle) containing the synthetic SP-C as the AD vehicle in the transnasal/mucosal vaccine were evaluated based on results of significant difference test of the levels.

In the nasal wash, an IgA production amount of the artificial surfactant-mixed vaccine administration group was significantly increased to a level almost identical with that of the positive control SURFACTEN (Pulmonary Surfactant)-mixed vaccine administration group. Also, IgG production that had not been detected in the AD vehicle-free vaccine group was detected (FIG. 4).

Figure 4:
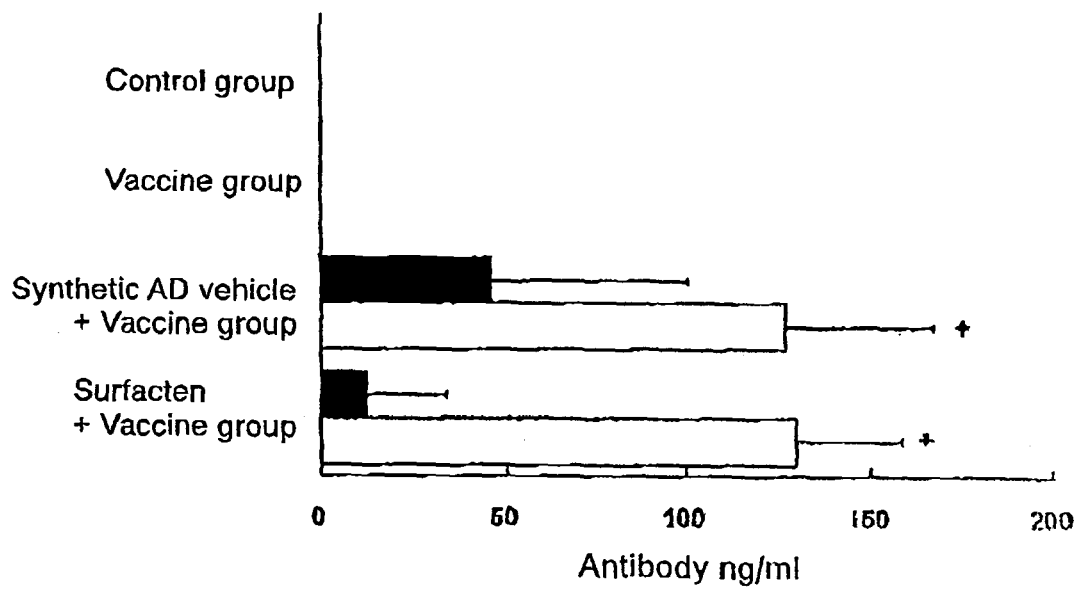
FIG. 4 A graph showing production amounts of anti-influenza IgA and IgG antibodies in nasal wash specimens of mice of a control group (no vaccine administration), a vaccine administration group (AD vehicle-free vaccine), an artificial synthetic surfactant (a variation of synthetic AD vehicle)-added vaccine administration group, and a SURFACTEN (Pulmonary Surfactant)-added vaccine administration group.
Figure 5:
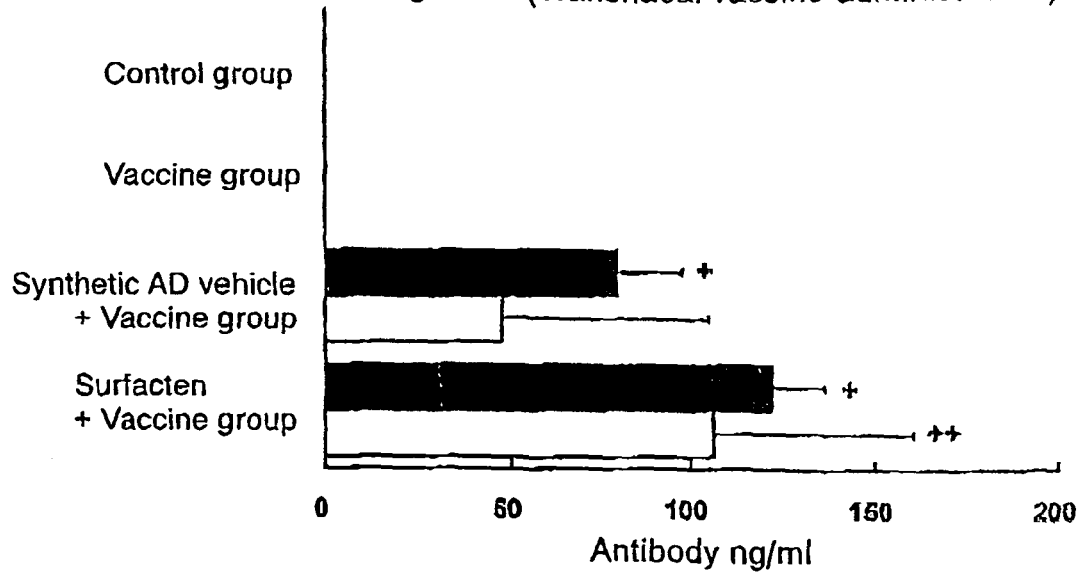
Figure 6:
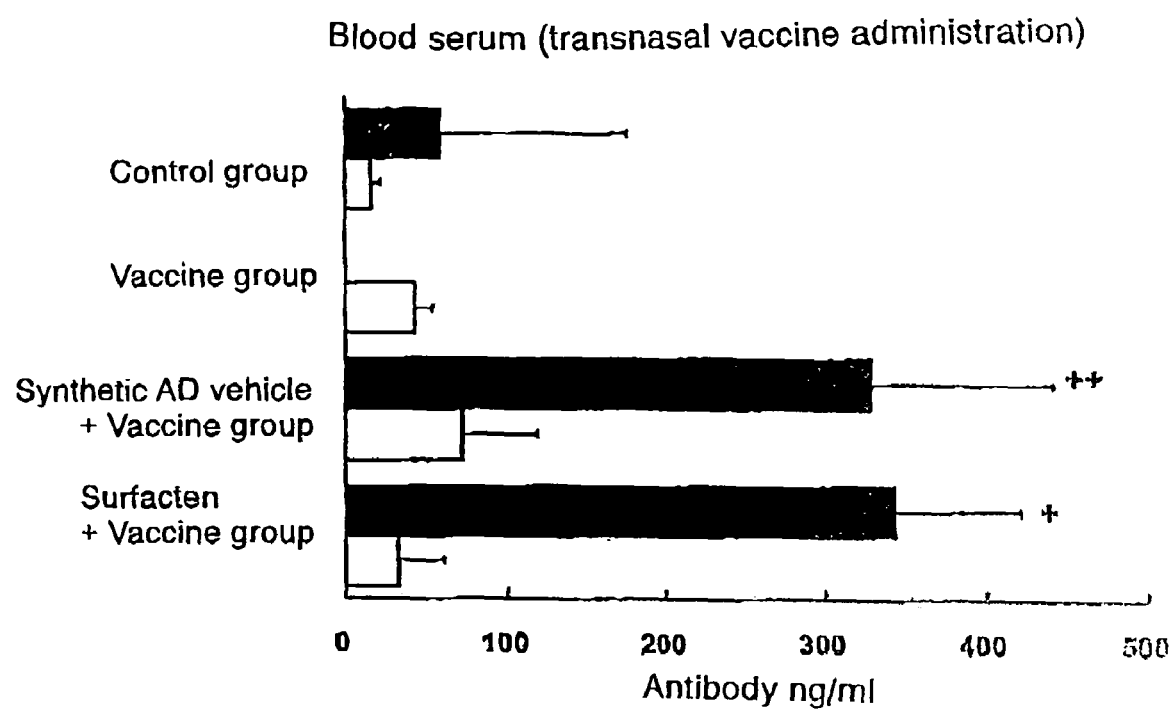

In FIGS. 4 to 6, □ indicates an IgA production amount, ■ indicates an IgG production amount, number of mice of a vaccine administration group is n=4, an average value is ±SD (standard deviation), significance level to the Ad vehicle-free vaccine administration group, + indicates $p<0.01$; and ++ indicates $p<0.05$.

In the lung wash, an IgG production amount of the artificial surfactant-mixed vaccine administration group was significantly increased like that of the positive control SURFACTEN (Pulmonary Surfactant)-mixed vaccine administration group. Also, though IgA production was detected, no significant difference between the production amount and that of the AD vehicle-free vaccine administration group was observed. However, since no significant difference was observed between the IgA production and the SURFACTEN (Pulmonary Surfactant)-mixed vaccine administration group, it was evaluated that the IgA production induction capacity of the artificial surfactant-mixed vaccine was similar to that of the positive control SURFACTEN (Pulmonary Surfactant)-mixed vaccine (FIG. 5).

In the blood, an IgG production amount of the artificial surfactant-mixed vaccine administration group was significantly increased to a level almost identical with that of the positive control SURFACTEN (Pulmonary Surfactant)-mixed vaccine administration group (FIG. 6).

Based on the above results, it was judged that the artificial synthetic surfactant has induction capability for both of mucosal immunity and humoral immunity like the cow-derived SURFACTEN (Pulmonary Surfactant).

EXAMPLE 3

1. Sample

Artificial surfactant drug: Surfacten (ST) was purchased from Mitsubishi Pharma Corporation.

Influenza Split Vaccine: A/New York/55/2004 (H3N2), A/New Caledonia/20/99 (H1N1), B/Shanghai/361/2002 were obtained from Osaka University Research Institute for Microbial Disease.

A synthetic surfactant Preparation substrate: DPPC (dipalmitoylphosphatidylcholine) was obtained from Wako Pure Chemical Industries, Inc. and Sigma; E-PG (egg-phosphatidylglycerol) was obtained from Avanti and Sigma; and PA (palmitic acid) was obtained from Wako Pure Chemical Industries, Inc.

Synthetic peptides were obtained from Gliner, Hayashi Kasei Co., Ltd., and the like. The synthetic peptides were SP-B(1-25) (SEQ ID NO: 21), SP-B(20-60) (SEQ ID NO: 22), SP-B(64-80) (SEQ ID NO: 23), SP-B(1-60) (SEQ ID NO: 24), SP-C(1-19) (SEQ ID NO: 25), synthetic peptide KL-4 which is under development and study as a respiratory disorder therapeutic drug (SEQ ID NO: 26), SP-CL(7-28) (SEQ ID NO: 27), SP-C33 (SEQ ID NO: 28), SP-C(FFI) (SEQ ID NO: 29), and SP-C(KLS) (SEQ ID NO: 30).

Protein and Phospholipid Measurement Kit: BCA™ (bicinchoninic acid) Protein Assay Kit was purchased from PIERCE, and Phospholipid C Test Wako was purchased from Wako Pure Chemical Industries, Inc.

2. Method

1) Preparation of Synthetic AD Vehicle

Each of the synthetic peptides was dissolved into an appropriate solvent. The hardly-soluble synthetic peptide was dissolved into TFA at a concentration of 5 to 20 mg/ml. DPPC, e-PG, and a PA lipid mixture (75:25:10; w/w/w) (hereinafter referred to as three-lipid mixture liquid) dissolved into a chloroform/methanol (2:1, v/v) mixture liquid was added to the synthetic peptide (0.6 to 2.0% (mol) with respect to phospholipid (PL)) dissolved into TFA. The mixture liquid was dried under a reduced pressure by a decompression concentrator. A 10%-ethanol solution was added to the dried matter, and pH thereof was adjusted to 6 to 7 with a N—NaOH solution, followed by heating at 42° C. to 45° C. for 3 to 10 minutes. After cooling, the concentration of the mixture was adjusted to 1 to 10 mg Pl/mL, and 1 to 5 mg PL equivalent amount was distributed and freeze-dried. The thus-obtained freeze-dried matter, i.e. the synthetic AD vehicle, was suspended into a normal saline solution to be used for a test for coupling to the vaccines.

Specifically, the following AD vehicles (synthetic surfactant: synthetic AD vehicle ST) were prepared.

(1) Preparation of Synthetic AD Vehicle SSF-14

0.27 mg of the synthetic peptide SP-B(1-25) was dissolved into TFA at a concentration of 5 mg/ml. The three-lipid mixture liquid dissolved into CM mixture liquid was added to the synthetic peptide dissolved into TFA in an amount of 0.6% (mol) with respect to the phospholipid of the lipid mixture, and the thus-obtained mixture was dried under a reduced pressure by a decompression concentrator. A 10%-ethanol solution was added to the dried matter, and pH thereof was adjusted to pH 6 to 7 with a N—NaOH solution, followed by heating at 42° C. to 45° C. for 3 minutes. After the solution was left to cool, a phospholipid concentration thereof was adjusted to 2 mg/mL and distributed to 1.5 mL-microtubes by an amount equivalent to 1 to 5 mg PL, followed by freeze-drying to prepare SSF-14.

(2) Preparation of Synthetic AD Vehicles SSF-28, SSF-30, SSF-24, and SSF-43

In the same manner as described above, SSF-28, SSF-30, SSF-24, AND SSF-43 were prepared by using the synthetic peptide SP-B(1-60), SP-B(20-60), SP-B(64-80), and SP-C(1-19), respectively.

(3) Preparation of Synthetic AD Vehicles SSF-44 to SSF-48

In the same manner as descried above, SSF-45, SSF-44, SSF-46, SSF-47, and SSF-48 were prepared by using KL-4, SP-CL(7-27), SP-C33, SP-C(FFI), and SP-C(KLS), respectively.

(4) Preparation of Synthetic AD Vehicle SSF-41 Containing SP-B and SP-C

The synthetic peptides SP-B(64-80) and SP-C(1-35) were dissolved into TFA at a concentration of 5 mg/mL. The three-lipid mixture was added to the synthetic peptides dissolved into TFA in an amount of 0.6% (mol) with respect to phospholipid of the three-lipid mixture. After that, the operation described above was performed to prepare SSF-41.

2) Test for Coupling AD Vehicle/Synthetic AD Vehicle to Vaccine (1) Test for Coupling AD Vehicle Surfactant (AD Vehicle ST) to Vaccine A suspension test was performed by setting: an AD vehicle concentration to 0.5 mg/mL, a vaccine concentration to 0.05 mg/mL, a ratio between the concentrations to 10:1, and a liquid amount to 0.4 mL scale.

A normal saline solution was added to ST to achieve a concentration of 30 mg/mL, followed by pipetting to obtain a suspension. 7 μL of the suspension was withdrawn into an Eppendorf tube, and 382 μL of a normal saline solution was added thereto, followed by a supersonic wave treatment by using Digital SONIFIER 250D (product of Branson) at an ice cool temperature for one minute. Subsequently, 11 μL of a vaccine solution (A/New Calcdonia/20/99(H1N1), 1.78 mg Prot/mL) was added to the suspension, followed by a supersonic wave treatment at an ice cool temperature for 3 minutes. After that, the solution was left to stand at a room temperature for 2 hours, during which inverted mild mixing was performed every 30 minutes for 3 to 5 times.

The AD vehicle ST-Vaccine mixture was centrifuged by using High Speed Refrigated micro centrifuge (Tomy MX 301) at a temperature of 4° C. to 5° C. at 20,000×g for 15 minutes. From the thus-obtained supernatant, 25 μL was separated to be used for measurement of a vaccine amount as a protein mass by using BCA™ (bicinchoninic acid) Protein Assay Kit.

Ratios of coupling of the three vaccines (A/New York, A/new Calcdonia, and B/Shanghai) to the AD vehicle ST were 60% to 70%.

(2) Test for Coupling Synthetic AD Vehicle Containing SP-B Fragment to Vaccine

In place of the AD vehicle ST of (1), synthetic AD vehicles SSF-14, SSF-30, and SSF-24 were used. Also, the vaccine used for the test was A/New Calcdonia.

A coupling test was performed by setting: a synthetic AD vehicle concentration (calculated in terms of phospholipid measured using Phosphlipid C Test Wako (Wako Pure Chemical Industries, Ltd.; 433-36201) to 2.5 mg/mL, a vaccine concentration to 0.05 mg/mL, a ratio between the concentrations to 50:1, and a liquid amount to 0.4 mL scale and in accordance with (1).

Results are shown in Table 1. A coupling ratio of the vaccine to SSF-14 was just under 60%, and coupling ratios of SSF-24 and SSF-30 were 90% or more.

(3) Test for Coupling Synthetic AD Vehicle Containing SP-C Fragment to Vaccine

A coupling ratio of SSF-43 to the vaccine (A/New Calcdonia) was measured.

A coupling test was performed by setting: a synthetic AD vehicle concentration (calculated in terms of phospholipid) to 0.5 mg/mL, a vaccine concentration to 0.05 mg/mL, a ratio between the concentrations to 10:1, and a liquid amount to 0.4 mL scale and in accordance with (1).

Results are shown in Table 2. A coupling ratio of the vaccine to SSF-43 was about 80%.

(4) Test for Coupling Synthetic AD Vehicle SSF-28 to Various Vaccines

A coupling test was performed by using SSF-28 as the synthetic AD vehicle and using A/New Calcdonia/20/99 (H1N1), A/New York/55/2004(H3N2), and B/Shanghai/361/2002 as the vaccines.

As a result, as shown in Table 3, coupling ratios of the vaccines to SSF-28 were about 60% or more.

(4) Test for Coupling Synthetic AD Vehicles SSF-44 to SSF-48 to Vaccine

A coupling test was performed by using SSF-45, SSF-44, SSF-46, SSF-47, and SSF-48 as the synthetic AD vehicles and in the same manner as described above.

As shown in Table 2, coupling ratios of the vaccine to the synthetic surfactants were about 60% or more.

TABLE 1

Coupling Test of Synthetic AD Vehicles Containing Synthetic Peptide and Influenza Vaccine

| Synthetic AD Vehicle | Peptide | Coupling Ratio (%) |
|---|---|---|
| SSF-14 | SP-B(1-25) | 57.0 |
| SSF-30 | SP-B(20-60) | 91.3 |
| SSF-24 | SP-B(64-80) | 91.3 |
| SSF-41 | SP-B(64-80) + SP-C(1-35) | 85.1 |

TABLE 2

Coupling Test of Synthetic AD Vehicles Containing Synthetic Peptide and Influenza Vaccine

| Synthetic AD Vehicle | Peptide | Coupling Ratio (%) |
|---|---|---|
| SSF-43 | SP-C(1-19) | 78.9 |
| SSF-45 | KL-4 | 64.8 |
| SSF-44 | SP-CL(7-28) | 72.8 |
| SSF-46 | SP-C33 | 76.2 |
| SSF-47 | SP-C(FFI) | 86.9 |
| SSF-48 | SP-C(KLS) | 66.3 |

TABLE 3

Coupling Test of Various Influenza Vaccines and Synthetic AD Vehicle SSF-28

| Influenza Vaccine | Synthetic AD Vehicle | Peptide | Coupling Ratio (%) |
|---|---|---|---|
| A/New York | SSF-28 | SP-B(1-60) | 64.4 |
| A/New Caledonia | | | 83.0 |
| B/Shanghai | | | 87.9 |

EXAMPLE 4

The nasal mucosa lymphatic tissue varies greatly depending on animal specie. Though a multiple of lymphatic tissues corresponding to Peyer's Patches of the intestine exists at the nasal mucosa of mice and rats, such lymphatic tissue does not exist at the human nasal mucosa, and it is difficult to mention that the experimental results of the transnasal mucosal vaccine for mice and rats are directly applicable to human. The lymphatic tissue of the human nostrils and pharynx consists mainly of Waldeyer's ring formed of the lymphatic tissues of tonsils and adenoid, and the animal having the lymphatic tissue relatively similar to the tissue is a pig. Accordingly, based on the results of the AD vehicle obtained on mice, the AD vehicle effect was investigated by using minipigs as a preclinical test assuming a human therapy to detect an administration amount, an administration method, and an adverse effect of the AD vehicle in the clinical test.

1) Sample and Method (1) Minipigs

Postweaning Minipigs of 1 to 2 month-year-old (weight: 2.2 to 6.6 kg) were used. Three subjects were used for one group, with which absence of abnormality was confirmed by testing 22 kinds of viruses, bacteria, parasites, and the like with which pigs are ordinarily infected.

(2) Virus Antigen

A split antigen of A/New Calcdonia/20/99(H1N1) was used.

(3) Surfactant Preparation

SURFACTEN™ (Pulmonary Surfactant) (AD vehicle ST) purchased from Mitsubishi Pharma Corporation was used.

(4) Protein and Phospholipid Measurement Kits

BCA™ (bicinchoninic acid) Protein Assay Kit was purchased from PIERCE, and Phospholipid C Test Wako was purchased from Wako Pure Chemical Industries, Inc.

2) Method (1) Inoculation Method and Sample Collection Method

Vaccine inoculation, blood collection, and nasal mucus collection were conducted under anesthesia. In order to calculate an anesthetic dose, weights of the minipigs were measured in advance of the anesthesia, and Domitol (product of Meiji Seika Kaisha, Ltd.) and Dormicam (product of Astellas Pharma Inc.) were mixed to be used for the anesthesia. Blood was collected from the venous cavity. Collection of nasal mucus was conducted by wiping the interior of the right and left nostrils with a sterilized cotton swab and dipping the cotton swab into 2 ml of a normal saline solution, followed by squeezing the cotton swab. A part of the nasal mucus was immediately subjected to cytopathologic diagnosis to investigate presence/absence of an inflammation reaction in the nostrils.

Weights and body temperatures were measured once a week, and health states were recorded twice a day by visual inspection.

(2) Measurement of Antigen-Specific Antibody Value

A measurement of an antigen specific antibody was conducted in accordance with the antigen specific antibody measurement in mouse and by employing an enzyme antibody technique (ELISA) using anti-pig IgA and IgG secondary antibodies.

3) Results

The split antigen of influenza A/New Calcdonia/20/99 (H1N1) was coupled to the AD vehicle ST to be suspended into 100 μl of a normal saline solution. The suspension was administered in the form of nasal drops to the minipigs (NIBS) with which no abnormality was detected by an ordinary pathogen test to measure production amounts of the antibodies (IgA, IgG) specific to the vaccine.

A booster administration was performed in such a manner that an administration in the same manner as the initial administration was performed at 4 weeks after the initial administration, and the measurement was ended at 2 weeks after the booster administration. Antigen amounts were detected in 5 groups of 0.3 μg/Kg, 1.5 μg/Kg, 4.5 μg/Kg, 15 μg/Kg, and 30 μg/Kg. For measurement of antibody value, a nasal mucus was measured for evaluating a local mucosal immunity, and a blood antibody production amount was measured for evaluating a systemic immunity.

As a result, the nasal mucus and the blood IgA and IgG values were scarcely changed after the 0.3 to 30 μg/Kg transnasal administration of the split influenza antigen alone or slightly increased to be short of the effective infection prevention antibody concentration (equal to or more than 40 antibodies of antigen-specific IgG/IgA). With the transnasal administration of the suspension wherein the split influenza antigen and the AD vehicle ST are coupled to each other by adding to the antigen the AD vehicle ST as an adjuvant in an amount (weight ratio) 10 times of the antigen, the IgA-specific antibody was particularly induced in the nasal mucus, while the IgG-specific antibody was particularly induced in the blood, depending on the administered antigen amount (0.3 to 30 mg/Kg). Particularly, with the antigen amount of 4.5 to 30 μg/Kg, the antigen-specific antibodies were induced to an antibody value of 200 to 800 depending on the administered antigen amount, and, thus, the effective adjuvant effect of the AD vehicle ST was proved. The IgA antibody value and IgG antibody value of the vaccine-specific antibodies defined herein was obtained by measuring the dilution degree that caused the value before the vaccine administration by setting an average of measurement values indicated as a result of the reaction between the vaccine antigen and the nasal mucus/blood before the vaccine administration as a reference, and the thus-detected dilution degree was considered as the antigen-specific IgA IgG antibody values.

In the antibody production in the nasal mucus, the IgA was preferentially produced, and the IgA antibody value was 5 to 8 times of the IgG antibody value. Increase tendencies of the IgA antibody value and the IgG antibody value depending on the antigen amount were not different from each other by a large scale. The production of the antibodies in the nasal mucus after the initial administration was weak and considerably increased by the booster administration. IgG in the nasal mucus with the single use of the split influenza antigen was increased after the booster administration to a value that was about ten times that before the booster administration though the increase was relatively weak.

As the blood antibody production, the IgG antibody value was 1 to 1.6 times of the IgA antibody value to reveal that IgG is preferentially produced in the blood. Both of the antibodies were increased to the antibody values of 100 to 200 after the primary immunization, and both of the IgA and IgG antibody values after the booster administration were 4 times of the values before the booster administration. Blood IgG with the single use of the split influenza antigen was increased after the booster administration to a value that was about ten times that before the booster administration though the increase was relatively weak.

In each of the samples, infiltration of inflammatory cells as a nasal inflammatory reaction was not observed.

INDUSTRIAL APPLICABILITY

The AD vehicle according to this invention enables safe administration or inoculation of an arbitrary vaccine antigen, a toxoid, an allergen, a drug, and the like which is performed transmucosally, transdermally, or the like. By adjusting a weight ratio V/A between the AD vehicle amount (V) and a substance to be mounted on the AD vehicle, such as the antigen amount (A), it is possible to adjust an antibody production induction function of the AD vehicle. More specifically, the AD vehicle preferentially and selectively induces IgA production when the V/A is about 1 or less and induces production of both of IgA and IgG when the V/A is adjusted to exceed 1. In the case of transnasally inoculating a relatively large amount of a vaccine antigen (15 mg/Kg or more), both of IgA for mucosal immunization and IgG for systemic immunization are induced irrespective of the V/A weight ratio. Therefore, the AD vehicle is widely useful as a vehicle or as a means for delivery and transportation of an active ingredient of a transnasal/mucosal vaccine, a therapeutic/prophylactic agent for allergy, and the like and is usable in the industrial fields of pharmaceutical agents according to vaccine and allergy therapy, veterinary, fishery, and the like.

The invention claimed is:

1. A mucosal vaccine, which comprises an inactivated antigen (A) from influenza virus and an antigen-drug vehicle, in which the antigen-drug vehicle is a complex of:
   lipids and a peptide consisting of the amino acid sequence of SEQ ID NO: 20
   wherein when a weight ratio V/A between a dry mass of the vehicle (V) and a dry mass of the antigen (A) exceeds about one, both IgA and IgG antibody production is induced, and when said weight ratio V/A is about one or less, IgA antibody production is induced and wherein the lipids consists of a mixture of dipalmitoylphosphatidylcholine, phosphatidylglycerol and palmitic acid.

2. A method for inducing a mucosal immunity, comprises adjusting the weight ratio V/A between the vehicle amount (V) and the antigen amount (A) set forth in claim 1 to about one to use a conversion switch from selective production of IgA antibody to production of both of IgA and IgG antibodies and administering the adjusted vaccine.